United States Patent
Cross et al.

(10) Patent No.: US 7,913,688 B2
(45) Date of Patent: Mar. 29, 2011

(54) INHALATION DEVICE FOR PRODUCING A DRUG AEROSOL

(75) Inventors: Stephen Cross, Alamo, CA (US); Craig C. Hodges, Walnut Creek, CA (US); Ron L. Hale, Woodside, CA (US); Peter M. Lloyd, Walnut Creek, CA (US); Daniel J. Myers, Mountain View, CA (US); Reynaldo J. Quintana, Redwood City, CA (US); Joshua D. Rabinowitz, Mountain View, CA (US); Curtis Tom, San Mateo, CA (US); Martin J. Wensley, San Francisco, CA (US)

(73) Assignee: Alexza Pharmaceuticals, Inc., Mountain View, CA (US)

( * ) Notice: Subject to any disclaimer, the term of this patent is extended or adjusted under 35 U.S.C. 154(b) by 0 days.

(21) Appl. No.: 10/442,385

(22) Filed: May 20, 2003

(65) Prior Publication Data
US 2004/0099266 A1 May 27, 2004

Related U.S. Application Data

(60) Provisional application No. 60/429,776, filed on Nov. 27, 2002, provisional application No. 60/429,586, filed on Nov. 27, 2002.

(51) Int. Cl.
*A61M 15/08* (2006.01)
*F23D 11/00* (2006.01)
*F23D 14/00* (2006.01)
(52) U.S. Cl. .............. 128/203.26; 128/203.24
(58) Field of Classification Search ............ 128/202.21, 128/203.26, 203.27, 204.17, 200.14, 200.22, 128/203.12, 203.24
See application file for complete search history.

(56) References Cited

U.S. PATENT DOCUMENTS 1,239,634 A * 9/1917 Stuart ................ 128/203.26
(Continued)

FOREIGN PATENT DOCUMENTS

CA 2152684 1/1996
(Continued)

OTHER PUBLICATIONS

Nieminen et al., "Aerosol Deposition in Automatic Dosimeter Nebulization", 1987, Eur. J. Respir. Dis., 71, 145-152.*
(Continued)

*Primary Examiner* — Justine R Yu
*Assistant Examiner* — Kristen C Matter
(74) *Attorney, Agent, or Firm* — Swanson & Bratschun, L.L.C.

(57) ABSTRACT

A device for delivering a drug by inhalation is disclosed. The device includes a body defining an interior flow-through chamber having upstream and downstream chamber openings, and a drug supply unit contained within the chamber for producing, upon actuation, a heated drug vapor in a condensation region of the chamber. Gas drawn through the chamber region at a selected gas-flow rate is effective to form drug condensation particles from the drug vapor having a selected MMAD between 0.02 and 0.1 MMAD or between 1 and 3.5 μm. A gas-flow control valve disposed upstream of the unit functions to limit gas-flow rate through the condensation region to the selected gas-flow rate. An actuation switch in the device activates the drug-supply unit, such that the drug-supply unit can be controlled to produce vapor when the gas-flow rate through the chamber is at the selected flow rate.

51 Claims, 8 Drawing Sheets

U.S. PATENT DOCUMENTS

| | | | |
|---|---|---|---|
| 1,535,486 A | 4/1925 | Lundy | |
| 1,803,334 A | 5/1931 | Lehmann | |
| 1,864,980 A | 6/1932 | Curran | |
| 2,084,299 A * | 6/1937 | Borden | 128/203.27 |
| 2,086,140 A * | 7/1937 | Silten | 128/203.14 |
| 2,230,753 A | 2/1941 | Klavehn et al. | |
| 2,230,754 A | 2/1941 | Klavehn et al. | |
| 2,243,669 A | 5/1941 | Clyne | |
| 2,309,846 A * | 2/1943 | Holm | 128/203.27 |
| 2,469,656 A | 5/1949 | Lienert | |
| 2,714,649 A | 8/1955 | Critzer | |
| 2,741,812 A | 4/1956 | Andre | |
| 2,761,055 A | 8/1956 | Ike | |
| 2,887,106 A | 5/1959 | Robinson | |
| 2,898,649 A | 8/1959 | Murray | |
| 2,902,484 A | 9/1959 | Horclois | |
| 3,043,977 A | 7/1962 | Morowitz | |
| 3,080,624 A | 3/1963 | Webber, III | |
| 3,164,600 A | 1/1965 | Janssen et al. | |
| 3,169,095 A | 2/1965 | Thiel et al. | |
| 3,200,819 A | 8/1965 | Gilbert | |
| 3,219,533 A | 11/1965 | Mullins | |
| 3,282,729 A | 11/1966 | Richardson et al. | |
| 3,296,249 A | 1/1967 | Bell | |
| 3,299,185 A | 1/1967 | Oda et al. | |
| 3,371,085 A | 2/1968 | Reeder et al. | |
| 3,393,197 A | 7/1968 | Pachter | |
| 3,433,791 A | 3/1969 | Bentley et al. | |
| 3,560,607 A | 2/1971 | Hartley et al. | |
| 3,701,782 A | 10/1972 | Hester | |
| 3,749,547 A | 7/1973 | Gregory et al. | |
| 3,763,347 A | 10/1973 | Whitaker et al. | |
| 3,773,995 A | 11/1973 | Pachter et al. | |
| 3,831,606 A | 8/1974 | Damani | |
| 3,842,828 A * | 10/1974 | Bird | 128/200.14 |
| 3,847,650 A | 11/1974 | Gregory et al. | |
| 3,864,326 A | 2/1975 | Babington | |
| 3,894,040 A | 7/1975 | Buzby, Jr. | |
| 3,909,463 A | 9/1975 | Hartman | |
| 3,930,796 A | 1/1976 | Haensel | |
| 3,943,941 A | 3/1976 | Boyd et al. | |
| 3,949,743 A | 4/1976 | Shanbrom | |
| 3,971,377 A | 7/1976 | Damani | |
| 3,982,095 A | 9/1976 | Robinson | |
| 3,987,052 A | 10/1976 | Hester, Jr. | |
| 4,008,723 A | 2/1977 | Borthwick et al. | |
| 4,020,379 A | 4/1977 | Manning | |
| 4,045,156 A | 8/1977 | Chu et al. | |
| 4,079,742 A | 3/1978 | Rainer et al. | |
| 4,104,210 A | 8/1978 | Coran et al. | |
| 4,121,583 A | 10/1978 | Chen | |
| 4,141,369 A | 2/1979 | Burruss | |
| 4,160,765 A | 7/1979 | Weinstock | |
| 4,166,087 A | 8/1979 | Cline et al. | |
| 4,183,912 A | 1/1980 | Rosenthale | |
| 4,184,099 A | 1/1980 | Lindauer et al. | |
| 4,190,654 A | 2/1980 | Gherardi et al. | |
| 4,198,200 A | 4/1980 | Fonda et al. | |
| RE30,285 E | 5/1980 | Babington | |
| 4,219,031 A | 8/1980 | Rainer et al. | |
| 4,229,447 A | 10/1980 | Porter | |
| 4,229,931 A | 10/1980 | Schlueter et al. | |
| 4,232,002 A | 11/1980 | Nogrady | |
| 4,236,544 A | 12/1980 | Osaka | |
| 4,251,525 A | 2/1981 | Weinstock | |
| 4,276,243 A | 6/1981 | Partus | |
| 4,280,629 A | 7/1981 | Slaughter | |
| 4,284,089 A | 8/1981 | Ray | |
| 4,286,604 A | 9/1981 | Ehretsmann et al. | |
| 4,303,083 A | 12/1981 | Burruss, Jr. | |
| 4,340,072 A | 7/1982 | Bolt et al. | |
| 4,346,059 A | 8/1982 | Spector | |
| 4,347,855 A | 9/1982 | Lanzillotti et al. | |
| 4,376,767 A | 3/1983 | Sloan | |
| 4,391,285 A | 7/1983 | Burnett et al. | |
| 4,423,071 A | 12/1983 | Chignac et al. | |
| 4,474,191 A | 10/1984 | Steiner | |
| 4,484,576 A | 11/1984 | Albarda | |
| 4,508,726 A | 4/1985 | Coleman | |
| 4,523,589 A * | 6/1985 | Krauser | 128/203.27 |
| 4,556,539 A | 12/1985 | Spector | |
| 4,566,451 A | 1/1986 | Badewien | |
| 4,588,425 A | 5/1986 | Usry et al. | |
| 4,588,721 A | 5/1986 | Mahan | |
| 4,591,615 A | 5/1986 | Aldred et al. | |
| 4,605,552 A | 8/1986 | Fritschi | |
| 4,627,963 A | 12/1986 | Olson | |
| 4,647,428 A | 3/1987 | Gyulay | |
| 4,647,433 A | 3/1987 | Spector | |
| 4,654,370 A | 3/1987 | Marriott, III et al. | |
| 4,683,231 A | 7/1987 | Glassman | |
| 4,693,868 A | 9/1987 | Katsuda et al. | |
| 4,708,151 A | 11/1987 | Shelar | |
| 4,714,082 A | 12/1987 | Banerjee et al. | |
| 4,722,334 A * | 2/1988 | Blackmer et al. | 128/203.16 |
| 4,734,560 A | 3/1988 | Bowen | |
| 4,735,217 A | 4/1988 | Gerth et al. | |
| 4,735,358 A | 4/1988 | Morita et al. | |
| 4,753,758 A | 6/1988 | Miller | |
| 4,755,508 A | 7/1988 | Bock et al. | |
| 4,756,318 A | 7/1988 | Clearman et al. | |
| 4,765,347 A | 8/1988 | Sensabaugh, Jr. et al. | |
| 4,771,795 A | 9/1988 | White et al. | |
| 4,774,971 A | 10/1988 | Vieten | |
| 4,793,365 A | 12/1988 | Sensabaugh, Jr. et al. | |
| 4,793,366 A | 12/1988 | Hill | |
| 4,800,903 A | 1/1989 | Ray et al. | |
| 4,801,411 A | 1/1989 | Wellinghoff et al. | |
| 4,814,161 A | 3/1989 | Jinks et al. | |
| 4,819,665 A | 4/1989 | Roberts et al. | |
| 4,848,374 A | 7/1989 | Chard et al. | |
| 4,852,561 A | 8/1989 | Sperry | |
| 4,853,517 A | 8/1989 | Bowen et al. | |
| 4,854,331 A | 8/1989 | Banerjee et al. | |
| 4,858,630 A | 8/1989 | Banerjee et al. | |
| 4,863,720 A | 9/1989 | Burghart et al. | |
| 4,881,541 A | 11/1989 | Eger et al. | |
| 4,881,556 A | 11/1989 | Clearman et al. | |
| 4,889,850 A | 12/1989 | Thornfeldt et al. | |
| 4,892,109 A | 1/1990 | Strubel | |
| 4,895,719 A | 1/1990 | Radhakrishnun et al. | |
| 4,906,417 A | 3/1990 | Gentry | |
| 4,911,157 A | 3/1990 | Miller | |
| 4,917,119 A * | 4/1990 | Potter et al. | 131/273 |
| 4,917,120 A | 4/1990 | Hill | |
| 4,917,830 A | 4/1990 | Ortiz et al. | |
| 4,922,901 A * | 5/1990 | Brooks et al. | 128/203.26 |
| 4,924,883 A | 5/1990 | Perfetti et al. | |
| 4,928,714 A | 5/1990 | Shannon | |
| 4,935,624 A | 6/1990 | Henion et al. | |
| 4,941,483 A | 7/1990 | Ridings et al. | |
| 4,947,874 A * | 8/1990 | Brooks et al. | 131/329 |
| 4,947,875 A | 8/1990 | Brooks et al. | |
| 4,950,664 A | 8/1990 | Goldberg | |
| 4,955,945 A | 9/1990 | Weick | |
| 4,959,380 A | 9/1990 | Wilson | |
| 4,963,289 A | 10/1990 | Ortiz et al. | |
| 4,968,885 A | 11/1990 | Willoughby | |
| 4,984,158 A * | 1/1991 | Hillsman | 128/200.14 |
| 4,989,619 A | 2/1991 | Clearman et al. | |
| 5,016,425 A | 5/1991 | Weick | |
| 5,017,575 A | 5/1991 | Golwyn | |
| 5,019,122 A | 5/1991 | Clearman et al. | |
| 5,020,548 A | 6/1991 | Farrier et al. | |
| 5,027,836 A | 7/1991 | Shannon et al. | |
| 5,033,483 A | 7/1991 | Clearman et al. | |
| 5,038,769 A | 8/1991 | Krauser | |
| 5,042,509 A | 8/1991 | Banerjee et al. | |
| 5,049,389 A | 9/1991 | Radhakrishnun | |
| 5,060,666 A | 10/1991 | Clearman et al. | |
| 5,060,667 A | 10/1991 | Strubel | |
| 5,060,671 A * | 10/1991 | Counts et al. | 131/329 |
| 5,067,499 A | 11/1991 | Banerjee et al. | |
| 5,072,726 A | 12/1991 | Mazloomdoost et al. | |
| 5,076,292 A | 12/1991 | Sensabaugh, Jr. et al. | |
| 5,093,894 A | 3/1992 | Deevi et al. | |
| 5,095,921 A | 3/1992 | Loose et al. | |

| | | | | | | |
|---|---|---|---|---|---|---|
| 5,099,861 A | 3/1992 | Clearman et al. | 5,592,934 A | 1/1997 | Thwaites | |
| 5,105,831 A | 4/1992 | Banerjee et al. | 5,593,792 A | 1/1997 | Farrier et al. | |
| 5,109,180 A | 4/1992 | Boultinghouse et al. | 5,605,146 A | 2/1997 | Sarela | |
| 5,112,598 A | 5/1992 | Biesalski | 5,605,897 A | 2/1997 | Beasley, Jr. et al. | |
| 5,118,494 A | 6/1992 | Schultz et al. | 5,607,691 A | 3/1997 | Hale et al. | |
| 5,119,834 A | 6/1992 | Shannon et al. | 5,613,504 A | 3/1997 | Collins et al. | |
| 5,126,123 A | 6/1992 | Johnson | 5,613,505 A | 3/1997 | Campbell et al. | |
| 5,133,368 A | 7/1992 | Neumann et al. | 5,619,984 A | 4/1997 | Hodson et al. | |
| 5,135,009 A | 8/1992 | Muller et al. | 5,622,944 A | 4/1997 | Hale et al. | |
| 5,137,034 A | 8/1992 | Perfetti et al. | 5,627,178 A | 5/1997 | Chakrabarti et al. | |
| 5,144,962 A | 9/1992 | Counts et al. | 5,649,554 A | 7/1997 | Sprinkel | |
| 5,146,915 A | 9/1992 | Montgomery | 5,655,523 A | 8/1997 | Hodson et al. | |
| 5,149,538 A | 9/1992 | Granger et al. | 5,656,255 A | 8/1997 | Jones | |
| 5,156,170 A | 10/1992 | Clearman et al. | 5,660,166 A | 8/1997 | Lloyd et al. | |
| 5,160,664 A | 11/1992 | Liu | 5,666,977 A * | 9/1997 | Higgins et al. | 131/194 |
| 5,164,740 A | 11/1992 | Ivri | 5,690,809 A | 11/1997 | Subramaniam et al. | |
| 5,166,202 A | 11/1992 | Schweizer | 5,694,919 A | 12/1997 | Rubsamen et al. | |
| 5,167,242 A | 12/1992 | Turner et al. | 5,718,222 A | 2/1998 | Lloyd et al. | |
| 5,177,071 A | 1/1993 | Freidinger et al. | 5,724,957 A | 3/1998 | Rubsamen et al. | |
| 5,179,966 A | 1/1993 | Losee et al. | 5,725,756 A | 3/1998 | Subramaniam et al. | |
| 5,186,164 A | 2/1993 | Raghuprasad | 5,733,572 A | 3/1998 | Unger et al. | |
| 5,192,548 A | 3/1993 | Velasquez et al. | 5,735,263 A | 4/1998 | Rubsamen et al. | |
| 5,224,498 A * | 7/1993 | Deevi et al. | 131/194 | 5,738,865 A | 4/1998 | Baichwal et al. | |
| 5,226,411 A | 7/1993 | Levine | 5,743,250 A | 4/1998 | Gonda et al. | |
| 5,229,120 A | 7/1993 | DeVincent | 5,743,251 A | 4/1998 | Howell et al. | |
| 5,229,382 A | 7/1993 | Chakrabarti et al. | 5,744,469 A | 4/1998 | Tran | |
| 5,240,922 A | 8/1993 | O'Neill | 5,747,001 A | 5/1998 | Wiedmann et al. | |
| 5,249,586 A * | 10/1993 | Morgan et al. | 131/194 | 5,756,449 A | 5/1998 | Andersen et al. | |
| 5,255,674 A * | 10/1993 | Oftedal et al. | 128/203.16 | 5,758,637 A | 6/1998 | Ivri et al. | |
| 5,261,424 A * | 11/1993 | Sprinkel, Jr. | 131/329 | 5,767,117 A | 6/1998 | Moskowitz et al. | |
| 5,264,433 A | 11/1993 | Sato et al. | 5,769,621 A | 6/1998 | Early et al. | |
| 5,269,327 A | 12/1993 | Counts et al. | 5,770,222 A | 6/1998 | Unger et al. | |
| 5,284,133 A | 2/1994 | Burns et al. | 5,771,882 A | 6/1998 | Psaros et al. | |
| 5,285,798 A | 2/1994 | Banerjee et al. | 5,776,928 A | 7/1998 | Beasley, Jr. | |
| 5,292,499 A | 3/1994 | Evans et al. | 5,804,212 A | 9/1998 | Illum | |
| 5,322,075 A | 6/1994 | Deevi et al. | 5,809,997 A * | 9/1998 | Wolf | 128/200.23 |
| 5,333,106 A | 7/1994 | Lanpher et al. | 5,817,656 A | 10/1998 | Beasley, Jr. et al. | |
| 5,345,951 A | 9/1994 | Serrano et al. | 5,819,756 A | 10/1998 | Mielordt | |
| 5,357,984 A | 10/1994 | Farrier et al. | 5,823,178 A | 10/1998 | Lloyd et al. | |
| 5,363,842 A * | 11/1994 | Mishelevich et al. | 128/200.14 | 5,823,180 A * | 10/1998 | Zapol | 128/200.24 |
| 5,364,838 A | 11/1994 | Rubsamen | 5,829,436 A | 11/1998 | Rubsamen et al. | |
| 5,366,770 A | 11/1994 | Wang | 5,833,891 A | 11/1998 | Subramaniam et al. | |
| 5,372,148 A * | 12/1994 | McCafferty et al. | 131/194 | 5,840,246 A | 11/1998 | Hammons et al. | |
| 5,376,386 A | 12/1994 | Ganderton et al. | 5,855,564 A | 1/1999 | Ruskewicz | |
| 5,388,574 A * | 2/1995 | Ingebrethsen | 128/203.17 | 5,855,913 A | 1/1999 | Hanes et al. | |
| 5,391,081 A | 2/1995 | Lampotang et al. | 5,865,185 A | 2/1999 | Collins et al. | |
| 5,399,574 A | 3/1995 | Robertson et al. | 5,874,064 A | 2/1999 | Edwards et al. | |
| 5,400,808 A | 3/1995 | Turner et al. | 5,874,481 A | 2/1999 | Weers et al. | |
| 5,400,969 A | 3/1995 | Keene | 5,875,776 A | 3/1999 | Vaghefi | |
| 5,402,517 A | 3/1995 | Gillett et al. | 5,878,752 A | 3/1999 | Adams et al. | |
| 5,408,574 A | 4/1995 | Deevi et al. | 5,884,620 A | 3/1999 | Gonda et al. | |
| 5,436,230 A | 7/1995 | Soudant et al. | 5,890,908 A | 4/1999 | Lampotang et al. | |
| 5,451,408 A | 9/1995 | Mezei et al. | 5,894,841 A * | 4/1999 | Voges | 128/203.12 |
| 5,455,043 A | 10/1995 | Fischel-Ghodsian | 5,904,900 A | 5/1999 | Bleuse et al. | |
| 5,456,247 A | 10/1995 | Shilling et al. | 5,906,202 A | 5/1999 | Schuster et al. | |
| 5,456,677 A | 10/1995 | Spector | 5,906,811 A | 5/1999 | Hersh | |
| 5,457,100 A | 10/1995 | Daniel | 5,907,075 A | 5/1999 | Subramaniam et al. | |
| 5,457,101 A | 10/1995 | Greenwood et al. | 5,910,301 A | 6/1999 | Farr et al. | |
| 5,459,137 A | 10/1995 | Andrasi et al. | 5,915,378 A | 6/1999 | Lloyd et al. | |
| 5,462,740 A | 10/1995 | Evenstad et al. | 5,918,595 A | 7/1999 | Olsson | |
| 5,468,936 A | 11/1995 | Deevi et al. | 5,928,520 A | 7/1999 | Haumesser | |
| 5,479,948 A | 1/1996 | Counts et al. | 5,929,093 A | 7/1999 | Pang et al. | |
| 5,501,236 A | 3/1996 | Hill et al. | 5,934,272 A | 8/1999 | Lloyd et al. | |
| 5,505,214 A | 4/1996 | Collins et al. | 5,934,289 A * | 8/1999 | Watkins et al. | 131/328 |
| 5,507,277 A | 4/1996 | Rubsamen et al. | 5,935,604 A | 8/1999 | Illum | |
| 5,511,726 A | 4/1996 | Greenspan et al. | 5,938,117 A | 8/1999 | Ivri | |
| 5,519,019 A | 5/1996 | Andrasi et al. | 5,939,100 A | 8/1999 | Albrechtsen et al. | |
| 5,525,329 A | 6/1996 | Snyder et al. | 5,941,240 A | 8/1999 | Gonda et al. | |
| 5,537,507 A | 7/1996 | Mariner et al. | 5,944,012 A | 8/1999 | Pera | |
| 5,538,020 A | 7/1996 | Farrier et al. | 5,957,124 A * | 9/1999 | Lloyd et al. | 128/200.22 |
| 5,540,959 A | 7/1996 | Wang | 5,960,792 A | 10/1999 | Lloyd et al. | |
| 5,543,434 A | 8/1996 | Weg | 5,970,973 A * | 10/1999 | Gonda et al. | 128/200.14 |
| 5,544,646 A | 8/1996 | Lloyd et al. | 5,971,951 A | 10/1999 | Ruskewicz | |
| 5,564,442 A | 10/1996 | MacDonald et al. | 5,985,309 A | 11/1999 | Edwards et al. | |
| 5,565,148 A | 10/1996 | Pendergrass | 5,993,805 A | 11/1999 | Sutton et al. | |
| 5,577,156 A | 11/1996 | Costello | 6,004,516 A | 12/1999 | Rasouli et al. | |
| 5,584,701 A | 12/1996 | Lampotang et al. | 6,004,970 A | 12/1999 | O'Malley et al. | |
| 5,586,550 A | 12/1996 | Ivri et al. | 6,008,214 A | 12/1999 | Kwon et al. | |
| 5,591,409 A | 1/1997 | Watkins | 6,008,216 A | 12/1999 | Chakrabarti et al. | |

| Patent | Kind | Date | Inventor | Class |
|---|---|---|---|---|
| 6,013,050 | A | 1/2000 | Bellhouse et al. | |
| 6,014,969 | A | 1/2000 | Lloyd et al. | |
| 6,014,970 | A | 1/2000 | Ivri et al. | |
| 6,041,777 | A | 3/2000 | Faithfull et al. | |
| 6,044,777 | A | 4/2000 | Walsh | |
| 6,048,550 | A | 4/2000 | Chan et al. | |
| 6,048,857 | A | 4/2000 | Ellinwood, Jr. et al. | |
| 6,050,260 | A | 4/2000 | Daniell et al. | |
| 6,051,257 | A | 4/2000 | Kodas et al. | |
| 6,051,566 | A | 4/2000 | Bianco | |
| 6,053,176 | A * | 4/2000 | Adams et al. | 131/329 |
| RE36,744 | E | 6/2000 | Goldberg | |
| 6,085,026 | A | 7/2000 | Hammons et al. | |
| 6,089,857 | A | 7/2000 | Matsuura et al. | |
| 6,090,212 | A | 7/2000 | Mahawili | |
| 6,090,403 | A | 7/2000 | Block et al. | |
| 6,095,134 | A | 8/2000 | Sievers et al. | |
| 6,095,153 | A | 8/2000 | Kessler et al. | |
| 6,098,620 | A | 8/2000 | Lloyd et al. | |
| 6,102,036 | A * | 8/2000 | Slutsky et al. | 128/203.15 |
| 6,113,795 | A | 9/2000 | Subramaniam et al. | |
| 6,117,866 | A | 9/2000 | Bondinell et al. | |
| 6,125,853 | A | 10/2000 | Susa et al. | |
| 6,126,919 | A | 10/2000 | Stefely et al. | |
| 6,131,566 | A | 10/2000 | Ashurst et al. | |
| 6,131,570 | A | 10/2000 | Schuster et al. | |
| 6,133,327 | A | 10/2000 | Kimura et al. | |
| 6,135,369 | A | 10/2000 | Prendergast et al. | |
| 6,136,295 | A | 10/2000 | Edwards et al. | |
| 6,138,683 | A | 10/2000 | Hersh et al. | |
| 6,140,323 | A | 10/2000 | Ellinwood, Jr. et al. | |
| 6,143,277 | A | 11/2000 | Ashurst et al. | |
| 6,143,746 | A | 11/2000 | Daugan et al. | |
| 6,149,892 | A | 11/2000 | Britto | |
| 6,155,268 | A | 12/2000 | Takeuchi | |
| 6,158,431 | A | 12/2000 | Poole | |
| 6,167,880 | B1 | 1/2001 | Gonda et al. | |
| 6,178,969 | B1 | 1/2001 | St. Charles | |
| 6,234,167 | B1 | 5/2001 | Cox et al. | |
| 6,241,969 | B1 | 6/2001 | Saidi et al. | |
| 6,250,301 | B1 | 6/2001 | Pate | |
| 6,255,334 | B1 | 7/2001 | Sands | |
| 6,263,872 | B1 | 7/2001 | Schuster et al. | |
| 6,264,922 | B1 | 7/2001 | Wood et al. | |
| 6,284,287 | B1 | 9/2001 | Sarlikiotis et al. | |
| 6,299,900 | B1 | 10/2001 | Reed et al. | |
| 6,300,710 | B1 | 10/2001 | Nakamori | |
| 6,306,431 | B1 | 10/2001 | Zhang et al. | |
| 6,309,668 | B1 | 10/2001 | Bastin et al. | |
| 6,309,986 | B1 | 10/2001 | Flashinski et al. | |
| 6,313,176 | B1 | 11/2001 | Ellinwood, Jr. et al. | |
| 6,325,475 | B1 | 12/2001 | Hayes et al. | |
| 6,376,550 | B1 | 4/2002 | Raber et al. | |
| 6,390,453 | B1 | 5/2002 | Frederickson et al. | |
| 6,408,854 | B1 | 6/2002 | Gonda et al. | |
| 6,413,930 | B1 | 7/2002 | Ratti et al. | |
| 6,420,351 | B1 | 7/2002 | Tsai et al. | |
| 6,431,166 | B2 | 8/2002 | Gonda et al. | |
| 6,443,152 | B1 | 9/2002 | Lockhart et al. | |
| 6,461,591 | B1 | 10/2002 | Keller et al. | |
| 6,491,233 | B2 | 12/2002 | Nichols | |
| 6,501,052 | B2 | 12/2002 | Cox et al. | |
| 6,506,762 | B1 | 1/2003 | Horvath et al. | |
| 6,514,482 | B1 | 2/2003 | Bartus et al. | |
| 6,516,796 | B1 | 2/2003 | Cox et al. | |
| 6,557,552 | B1 | 5/2003 | Cox et al. | |
| 6,561,186 | B2 | 5/2003 | Casper et al. | |
| 6,568,390 | B2 | 5/2003 | Nichols et al. | |
| 6,591,839 | B2 | 7/2003 | Meyer et al. | |
| 6,632,047 | B2 | 10/2003 | Vinegar et al. | |
| 6,648,950 | B2 | 11/2003 | Lee et al. | |
| 6,671,945 | B2 | 1/2004 | Gerber et al. | |
| 6,680,668 | B2 | 1/2004 | Gerber et al. | |
| 6,681,769 | B2 | 1/2004 | Sprinkel et al. | |
| 6,681,998 | B2 | 1/2004 | Sharpe et al. | |
| 6,682,716 | B2 | 1/2004 | Hodges et al. | |
| 6,688,313 | B2 | 2/2004 | Wrenn et al. | |
| 6,694,975 | B2 * | 2/2004 | Schuster et al. | 128/203.26 |
| 6,701,921 | B2 * | 3/2004 | Sprinkel et al. | 128/203.26 |
| 6,701,922 | B2 * | 3/2004 | Hindle et al. | 128/203.27 |
| 6,715,487 | B2 | 4/2004 | Nichols et al. | |
| 6,716,415 | B2 | 4/2004 | Rabinowitz et al. | |
| 6,716,416 | B2 | 4/2004 | Rabinowitz et al. | |
| 6,716,417 | B2 | 4/2004 | Rabinowitz et al. | |
| 6,728,478 | B2 | 4/2004 | Cox et al. | |
| 6,729,324 | B2 * | 5/2004 | Casper et al. | 128/200.23 |
| 6,737,042 | B2 | 5/2004 | Rabinowitz et al. | |
| 6,737,043 | B2 | 5/2004 | Rabinowitz et al. | |
| 6,740,307 | B2 | 5/2004 | Rabinowitz et al. | |
| 6,740,308 | B2 | 5/2004 | Rabinowitz et al. | |
| 6,740,309 | B2 | 5/2004 | Rabinowitz et al. | |
| 6,743,415 | B2 | 6/2004 | Rabinowitz et al. | |
| 6,759,029 | B2 | 7/2004 | Hale et al. | |
| 6,772,756 | B2 * | 8/2004 | Shayan | 128/203.26 |
| 6,772,757 | B2 * | 8/2004 | Sprinkel, Jr. | 128/203.26 |
| 6,776,978 | B2 | 8/2004 | Rabinowitz et al. | |
| 6,779,520 | B2 * | 8/2004 | Genova et al. | 128/200.22 |
| 6,780,399 | B2 | 8/2004 | Rabinowitz et al. | |
| 6,780,400 | B2 | 8/2004 | Rabinowitz et al. | |
| 6,783,753 | B2 | 8/2004 | Rabinowitz et al. | |
| 6,797,259 | B2 | 9/2004 | Rabinowitz et al. | |
| 6,803,031 | B2 | 10/2004 | Rabinowitz et al. | |
| 6,805,853 | B2 | 10/2004 | Rabinowitz et al. | |
| 6,805,854 | B2 | 10/2004 | Hale et al. | |
| 6,814,954 | B2 | 11/2004 | Rabinowitz et al. | |
| 6,814,955 | B2 | 11/2004 | Rabinowitz et al. | |
| 6,855,310 | B2 | 2/2005 | Rabinowitz et al. | |
| 6,884,408 | B2 | 4/2005 | Rabinowitz et al. | |
| 6,994,843 | B2 | 2/2006 | Rabinowitz et al. | |
| 7,005,121 | B2 | 2/2006 | Rabinowitz et al. | |
| 7,005,122 | B2 | 2/2006 | Hale et al. | |
| 7,008,615 | B2 | 3/2006 | Rabinowitz et al. | |
| 7,008,616 | B2 | 3/2006 | Rabinowitz et al. | |
| 7,011,819 | B2 | 3/2006 | Hale et al. | |
| 7,011,820 | B2 | 3/2006 | Rabinowitz et al. | |
| 7,014,840 | B2 | 3/2006 | Hale et al. | |
| 7,014,841 | B2 | 3/2006 | Rabinowitz et al. | |
| 7,018,619 | B2 | 3/2006 | Rabinowitz et al. | |
| 7,018,620 | B2 | 3/2006 | Rabinowitz et al. | |
| 7,018,621 | B2 | 3/2006 | Hale et al. | |
| 7,022,312 | B2 | 4/2006 | Rabinowitz et al. | |
| 7,029,658 | B2 | 4/2006 | Rabinowitz et al. | |
| 7,033,575 | B2 | 4/2006 | Rabinowitz et al. | |
| 7,040,314 | B2 | 5/2006 | Nguyen et al. | |
| 7,045,118 | B2 | 5/2006 | Rabinowitz et al. | |
| 7,045,119 | B2 | 5/2006 | Rabinowitz et al. | |
| 7,048,909 | B2 | 5/2006 | Rabinowitz et al. | |
| 7,052,679 | B2 | 5/2006 | Rabinowitz et al. | |
| 7,052,680 | B2 | 5/2006 | Rabinowitz et al. | |
| 7,060,254 | B2 | 6/2006 | Rabinowitz et al. | |
| 7,060,255 | B2 | 6/2006 | Rabinowitz et al. | |
| 7,063,830 | B2 | 6/2006 | Rabinowitz et al. | |
| 7,063,831 | B2 | 6/2006 | Rabinowitz et al. | |
| 7,063,832 | B2 | 6/2006 | Rabinowitz et al. | |
| 7,067,114 | B2 | 6/2006 | Rabinowitz et al. | |
| 7,070,761 | B2 | 7/2006 | Rabinowitz et al. | |
| 7,070,762 | B2 | 7/2006 | Rabinowitz et al. | |
| 7,070,763 | B2 | 7/2006 | Rabinowitz et al. | |
| 7,070,764 | B2 | 7/2006 | Rabinowitz et al. | |
| 7,070,765 | B2 | 7/2006 | Rabinowitz et al. | |
| 7,070,766 | B2 | 7/2006 | Rabinowitz et al. | |
| 7,078,016 | B2 | 7/2006 | Rabinowitz et al. | |
| 7,078,017 | B2 | 7/2006 | Rabinowitz et al. | |
| 7,078,018 | B2 | 7/2006 | Rabinowitz et al. | |
| 7,078,019 | B2 | 7/2006 | Rabinowitz et al. | |
| 7,078,020 | B2 | 7/2006 | Rabinowitz et al. | |
| 7,087,216 | B2 | 8/2006 | Rabinowitz et al. | |
| 7,087,217 | B2 | 8/2006 | Rabinowitz et al. | |
| 7,087,218 | B2 | 8/2006 | Rabinowitz et al. | |
| 7,090,830 | B2 | 8/2006 | Hale et al. | |
| 7,094,392 | B2 | 8/2006 | Rabinowitz et al. | |
| 7,108,847 | B2 | 9/2006 | Rabinowitz et al. | |
| 7,115,250 | B2 | 10/2006 | Rabinowitz et al. | |
| 7,169,378 | B2 | 1/2007 | Rabinowitz et al. | |
| 7,402,777 | B2 | 7/2008 | Ron et al. | |
| 2001/0020147 | A1 | 9/2001 | Staniforth et al. | |
| 2001/0042546 | A1 | 11/2001 | Umeda et al. | |
| 2002/0031480 | A1 | 3/2002 | Peart et al. | |

| | | |
|---|---|---|
| 2002/0037828 A1 | 3/2002 | Wilson et al. |
| 2002/0058009 A1 | 5/2002 | Bartus et al. |
| 2002/0061281 A1 | 5/2002 | Osbakken et al. |
| 2002/0078955 A1 | 6/2002 | Nichols et al. |
| 2002/0086852 A1 | 7/2002 | Cantor |
| 2002/0097139 A1 | 7/2002 | Gerber et al. |
| 2002/0112723 A1 | 8/2002 | Schuster et al. |
| 2002/0117175 A1 | 8/2002 | Kottayil et al. |
| 2002/0176841 A1 | 11/2002 | Barker et al. |
| 2003/0004142 A1 | 1/2003 | Prior et al. |
| 2003/0015196 A1 | 1/2003 | Hodges et al. |
| 2003/0015197 A1 | 1/2003 | Hale et al. |
| 2003/0032638 A1 | 2/2003 | Kim et al. |
| 2003/0033055 A1 | 2/2003 | McRae et al. |
| 2003/0049025 A1 | 3/2003 | Neumann et al. |
| 2003/0051728 A1 | 3/2003 | Lloyd et al. |
| 2003/0062042 A1 | 4/2003 | Wensley et al. |
| 2003/0106551 A1 | 6/2003 | Sprinkel et al. |
| 2003/0118512 A1 | 6/2003 | Shen |
| 2003/0121906 A1 | 7/2003 | Abbott et al. |
| 2003/0131843 A1 | 7/2003 | Lu |
| 2003/0132219 A1 | 7/2003 | Cox et al. |
| 2003/0138508 A1 | 7/2003 | Novack et al. |
| 2003/0156829 A1 | 8/2003 | Cox et al. |
| 2003/0209240 A1 | 11/2003 | Hale et al. |
| 2004/0009128 A1 | 1/2004 | Rabinowitz et al. |
| 2004/0016427 A1 | 1/2004 | Byron et al. |
| 2004/0035409 A1 | 2/2004 | Harwig et al. |
| 2004/0055504 A1 | 3/2004 | Lee et al. |
| 2004/0081624 A1 | 4/2004 | Nguyen et al. |
| 2004/0096402 A1 | 5/2004 | Hodges et al. |
| 2004/0101481 A1 | 5/2004 | Hale et al. |
| 2004/0102434 A1 | 5/2004 | Hale et al. |
| 2004/0105818 A1 | 6/2004 | Every et al. |
| 2004/0105819 A1 | 6/2004 | Hale et al. |
| 2004/0234699 A1 | 11/2004 | Hale et al. |
| 2004/0234914 A1 | 11/2004 | Hale et al. |
| 2004/0234916 A1 | 11/2004 | Hale et al. |
| 2005/0034723 A1 | 2/2005 | Bennett et al. |
| 2005/0037506 A1 | 2/2005 | Hale et al. |
| 2005/0079166 A1 | 4/2005 | Damani et al. |
| 2005/0126562 A1 | 6/2005 | Rabinowitz et al. |
| 2005/0131739 A1 | 6/2005 | Rabinowitz et al. |
| 2005/0268911 A1 | 12/2005 | Cross et al. |
| 2006/0032496 A1 | 2/2006 | Hale et al. |
| 2006/0032501 A1 | 2/2006 | Hale et al. |
| 2006/0120962 A1 | 6/2006 | Rabinowitz et al. |
| 2006/0153779 A1 | 7/2006 | Rabinowitz et al. |
| 2006/0177382 A1 | 8/2006 | Rabinowitz et al. |
| 2006/0193788 A1 | 8/2006 | Hale et al. |
| 2006/0216243 A1 | 9/2006 | Rabinowitz et al. |
| 2006/0216244 A1 | 9/2006 | Rabinowitz et al. |
| 2006/0233717 A1 | 10/2006 | Hale et al. |
| 2006/0233718 A1 | 10/2006 | Rabinowitz et al. |
| 2006/0233719 A1 | 10/2006 | Rabinowitz et al. |
| 2006/0239936 A1 | 10/2006 | Rabinowitz et al. |
| 2006/0246011 A1 | 11/2006 | Rabinowitz et al. |
| 2006/0246012 A1 | 11/2006 | Rabinowitz et al. |
| 2006/0251587 A1 | 11/2006 | Rabinowitz et al. |
| 2006/0251588 A1 | 11/2006 | Rabinowitz et al. |
| 2006/0257328 A1 | 11/2006 | Rabinowitz et al. |
| 2006/0257329 A1 | 11/2006 | Rabinowitz et al. |
| 2006/0269486 A1 | 11/2006 | Rabinowitz et al. |
| 2006/0269487 A1 | 11/2006 | Rabinowitz et al. |
| 2006/0280692 A1 | 12/2006 | Rabinowitz et al. |
| 2006/0286042 A1 | 12/2006 | Rabinowitz et al. |
| 2006/0286043 A1 | 12/2006 | Rabinowitz et al. |
| 2007/0014737 A1 | 1/2007 | Rabinowitz et al. |
| 2007/0028916 A1 | 2/2007 | Hale et al. |
| 2007/0031340 A1 | 2/2007 | Hale et al. |
| 2007/0122353 A1 | 5/2007 | Hale et al. |
| 2007/0140982 A1 | 6/2007 | Every et al. |
| 2007/0178052 A1 | 8/2007 | Rabinowitz et al. |
| 2007/0286816 A1 | 12/2007 | Hale et al. |
| 2008/0110872 A1 | 5/2008 | Hale et al. |
| 2008/0175796 A1 | 7/2008 | Rabinowitz et al. |
| 2008/0216828 A1 | 9/2008 | Wensley |

FOREIGN PATENT DOCUMENTS

| | | |
|---|---|---|
| CN | 1082365 | 2/1994 |
| CN | 1176075 | 3/1998 |
| DE | 198 54 007 | 5/2000 |
| EP | 0 039 369 | 11/1981 |
| EP | 0 274 431 | 7/1988 |
| EP | 0 277 519 | 8/1988 |
| EP | 0 358 114 | 3/1990 |
| EP | 0 430 559 | 6/1991 |
| EP | 0 492 485 | 7/1992 |
| EP | 0 606 486 | 7/1994 |
| EP | 0 734 719 | 2/1996 |
| EP | 0 808 635 A3 * | 7/1998 |
| EP | 0 967 214 | 12/1999 |
| EP | 1 080 720 | 3/2001 |
| EP | 1 177 793 | 2/2002 |
| FR | 921 852 A | 5/1947 |
| FR | 2 428 068 A | 1/1980 |
| GB | 502 761 | 1/1938 |
| GB | 903 866 | 8/1962 |
| GB | 1 366 041 | 9/1974 |
| GB | 2 108 390 | 5/1983 |
| GB | 2 122 903 | 1/1984 |
| HU | 200105 B | 10/1988 |
| HU | 219392 B | 6/1993 |
| WO | WO 85/00520 | 2/1985 |
| WO | WO 88/08304 | 11/1988 |
| WO | WO 90/02737 | 3/1990 |
| WO | WO 90/07333 | 7/1990 |
| WO | WO 91/07947 | 6/1991 |
| WO | WO 91/18525 | 12/1991 |
| WO | WO 92/05781 | 4/1992 |
| WO | WO 92/15353 | 9/1992 |
| WO | WO 92/19303 | 11/1992 |
| WO | WO 93/12823 | 7/1993 |
| WO | WO 94/09842 | 5/1994 |
| WO | WO 94/16717 | 8/1994 |
| WO | WO 94/16757 | 8/1994 |
| WO | WO 94/16759 | 8/1994 |
| WO | WO 94/17369 | 8/1994 |
| WO | WO 94/17370 | 8/1994 |
| WO | WO 94/27576 | 12/1994 |
| WO | WO 94/27653 | 12/1994 |
| WO | WO 95/31182 | 11/1995 |
| WO | WO 96/00069 | 1/1996 |
| WO | WO 96/00070 | 1/1996 |
| WO | WO 96/00071 | 1/1996 |
| WO | WO 96/09846 | 4/1996 |
| WO | WO 96/10663 | 4/1996 |
| WO | WO 96/13161 | 5/1996 |
| WO | WO 96/13290 | 5/1996 |
| WO | WO 96/13291 | 5/1996 |
| WO | WO 96/13292 | 5/1996 |
| WO | WO 96/30068 | 10/1996 |
| WO | WO 96/31198 | 10/1996 |
| WO | WO 96/37198 | 11/1996 |
| WO | WO 97/16181 | 5/1997 |
| WO | WO 97/17948 | 5/1997 |
| WO | WO 97/23221 | 7/1997 |
| WO | WO 97/27804 | 8/1997 |
| WO | WO 97/31691 | 9/1997 |
| WO | WO 97/35562 | 10/1997 |
| WO | WO 97/36574 | 10/1997 |
| WO | WO 97/40819 * | 11/1997 |
| WO | WO 97/49690 | 12/1997 |
| WO | WO 98/02186 | 1/1998 |
| WO | WO 98/16205 | 4/1998 |
| WO | WO 98/22170 | 5/1998 |
| WO | WO 98/29110 | 7/1998 |
| WO | WO 98/31346 | 7/1998 |
| WO | WO 98/34595 | 8/1998 |
| WO | WO 98/36651 | 8/1998 |
| WO | WO 98/37896 | 9/1998 |
| WO | WO 99/04797 | 2/1999 |
| WO | WO 99/16419 | 4/1999 |
| WO | WO 99/24433 | 5/1999 |
| WO | WO 99/37347 | 7/1999 |
| WO | WO 99/37625 | 7/1999 |
| WO | WO 99/44664 | 9/1999 |

| | | |
|---|---|---|
| WO | WO 99/55362 | 11/1999 |
| WO | WO 99/59710 | 11/1999 |
| WO | WO 99/64094 | 12/1999 |
| WO | WO 00/00176 | 1/2000 |
| WO | WO 00/00215 | 1/2000 |
| WO | WO 00/00244 | 1/2000 |
| WO | WO 00/19991 | 4/2000 |
| WO | WO 00/27359 | 5/2000 |
| WO | WO 00/27363 | 5/2000 |
| WO | WO 00/28979 | 5/2000 |
| WO | WO 00/29053 | 5/2000 |
| WO | WO 00/29167 | 5/2000 |
| WO | WO 00/35417 | 6/2000 |
| WO | WO 00/38618 | 7/2000 |
| WO | WO 00/44350 | 8/2000 |
| WO | WO 00/44730 | 8/2000 |
| WO | WO 00/47203 | 9/2000 |
| WO | WO 00/51491 | 9/2000 |
| WO | WO 00/64940 | 11/2000 |
| WO | WO 00/66084 | 11/2000 |
| WO | WO 00/66106 | 11/2000 |
| WO | WO 00/66206 | 11/2000 |
| WO | WO 00/72827 | 12/2000 |
| WO | WO 00/76673 | 12/2000 |
| WO | WO 01/05459 | 1/2001 |
| WO | WO 01/13957 | 3/2001 |
| WO | WO 01/17568 | 3/2001 |
| WO | WO 01/19528 | 3/2001 |
| WO | WO 01/29011 | 4/2001 |
| WO | WO 01/32144 | 5/2001 |
| WO | WO 01/41732 | 6/2001 |
| WO | WO 01/43801 | 6/2001 |
| WO | WO 01/66064 | 9/2001 |
| WO | WO 01/95903 | 12/2001 |
| WO | WO 02/00198 | 1/2002 |
| WO | WO 02/24158 | 3/2002 |
| WO | WO 02/051466 | 7/2002 |
| WO | WO 02/056866 | 7/2002 |
| WO | WO 02/094234 | 11/2002 |
| WO | WO 03/037412 | 5/2003 |

OTHER PUBLICATIONS

The American Heritage Dictionary, 2nd College Edition, 1982, p. 1337.*
Office Action mailed Aug. 13, 2003 for U.S. Appl. No. 10/153,313, filed May 21, 2002 "Delivery of Benzodiazepines Through an Inhalation Route".
U.S. Appl. No. 11/687,466, filed Mar. 16, 2007, Zaffaroni et al.
U.S. Appl. No. 11/964,630, filed Dec. 26, 2007, Hale et al.
U.S. Appl. No. 12/111,188, filed Apr. 28, 2008, Hale et al.
U.S. Appl. No. 12/117,737, filed May 8, 2008, Hale et al.
U.S. Appl. No. 12/211,247, filed Sep. 16, 2008, Sharma et al.
U.S. Appl. No. 12/211,554, filed Sep. 16, 2008, Sharma et al.
U.S. Appl. No. 12/211,628, filed Sep. 16, 2008, Lei et al.
Office Action mailed Jan. 26, 2007 with respect to U.S. Appl. No. 10/057,198.
Office Action mailed Jul. 3, 2006 with respect to U.S. Appl. No. 10/057,198.
Office Action mailed Sep. 20, 2005 with respect to U.S. Appl. No. 10/057,198.
Office Action mailed Dec. 4, 2003 with respect to U.S. Appl. No. 10/057,198.
Office Action mailed Jan. 12, 2005 with respect to U.S. Appl. No. 10/057,197.
Office Action mailed Jun. 3, 2004 with respect to U.S. Appl. No. 10/057,197.
Office Action mailed Jun. 5, 2007 with respect to U.S. Appl. No. 10/057,197.
Office Action mailed Sep. 21, 2006 with respect to U.S. Appl. No. 10/057,197.
Office Action mailed Dec. 15, 2003 with respect to U.S. Appl. No. 10/057,197.
Office Action mailed Feb. 27, 2004 with respect to U.S. Appl. No. 10/146,080.
Office Action mailed Mar. 20, 2007 with respect to U.S. Appl. No. 10/146,080.
Office Action mailed Jun. 5, 2006 with respect to U.S. Appl. No. 10/146,080.
Office Action mailed Aug. 25, 2005 with respect to U.S. Appl. No. 10/146,080.
Office Action mailed Dec. 28, 2007 with respect to U.S. Appl. No. 10/146,080.
Office Action mailed Feb. 12, 2007 with respect to U.S. Appl. No. 10/146,086.
Office Action mailed Oct. 30, 2007 with respect to U.S. Appl. No. 10/146,086.
Office Action mailed Dec. 13, 2005 with respect to U.S. Appl. No. 10/146,086.
Office Action mailed Feb. 16, 2007 with respect to U.S. Appl. No. 10/146,088.
Office Action mailed Sep. 28, 2007 with respect to U.S. Appl. No. 10/146,088.
Office Action mailed Nov. 21, 2007 with respect to U.S. Appl. No. 10/146,088.
Office Action mailed Mar. 8, 2005 with respect to U.S. Appl. No. 10/718,982.
Anderson, M.E. (1982). "Recent Advances in Methodology and Concepts for Characterizing Inhalation Pharmacokinetic Parameters in Animals and Man," Drug Metabolism Reviews. 13(5):799-826.
Anonymous, (Jun. 1998) Guidance for Industry: Stability testing of drug substances and products, U.S. Department of Health and Human Services, FDA, CDER, CBER, pp. 1-110.
Bennett, R. L. et al. (1981). "Patient-Controlled Analgesia: A New Concept of Postoperative Pain Relief," Annual Surg. 195(6):700-705.
Benowitz (1994). "Individual Differences in Nicotine Kinetics and Metabolism in Humans," NIDA Research Monography, 2 pages.
BP: Chemicals Products-Barrier Resins (1999). located at <http://www.bp.com/chemicals/products/product.asp> (visited on Aug. 2, 2001), 8 pages.
Brand, P. et al. (Jun. 2000). "Total Deposition of Therapeutic Particles During Spontaneous and Controlled Inhalations," Journal of Pharmaceutical Sciences. 89(6):724-731.
Campbell, Fiona A. et al. (2001) "Are cannabinoids an effective and safe treatment option in the management of pain? A qualitative systemic review," BMJ, 323 pp. 1-6.
Carroll, M.E. et al. (1990), "Cocaine-Base Smoking in Rhesus Monkey: Reinforcing and Physiological Effects," Psychopharmacology (Berl) 102:443-450.
Cichewicz, Diana L. et al. (May 1999) "Enhancement of mu opioid antinociception by oral DELTA 9—tetrahydrocannabinol: Dose response analysis and receptor identification" Journal of Pharmacology and Experimental Therapeutics vol. 289 (2): 859-867.
Clark, A. and Byron, P. (1986). "Dependence of Pulmonary Absorption Kinetics on Aerosol Particle Size," Z. Erkrank. 166:13-24.
Dallas, C. et al. (1983). "A Small Animal Model for Direct Respiratory and Hemodynamic Measurements in Toxicokinetic Studies of Volatile Chemicals," Devlopments in the Science and Practice of Toxicology. Hayes, A. W. et al. eds., Elsevier Science Publishers, New York. pp. 419-422.
Darquenne, C. et al. (1997). "Aerosol Disperion in Human Lung: Comparison Between Numerical Simulations and Experiments for Bolus Tests," American Physiological Society. 969-974.
Database Biosis "Online!" Biosciences Information Service, Philadelphia, PA 1979, Knight, V. et al., "Amantadine aerosol in humans", database accession No. PREV 198069035552 abstract, &Antimicrobial Agents and Chemotherapy 16(5):572-578.
Database Biosis "Online!" Biosciences Information Service, Philadelphia, PA 1979, Wilson. S.Z. et al., "Amatadine Aerosol Particle A.erosol Generation and Delivery to Man" Database accession No. PREV198069008137, abstract & Proceedings of the Society for Experimental Biology and Medicine 161(3):350-354.
Database WPI, Section CH, Week 198941, Derwent Publications Ltd., London, GB; AN 1989-297792 AP002230849 & JP 01 221313 (Nippon Create 1(K), Sep. 4, 1989, abstract.
Davies, C. N. et al. (May 1972). "Breathing of Half-Micron Aerosols," Journal of Applied Physiology. 32(5):591-600.

Dershwitz, M., M.D., et al. (Sep. 2000). "Pharmacokinetics and Pharmacodynamics of Inhaled versus Intravenous Morphine in Healthy Volunteers," Anesthesiology. 93(3): 619-628.

Drugs Approved by the FDA—Drug Name: Nicotrol Inhaler (2000) located at <http://www.centerwatch.com/patient/drugs/dru202.html> (Visited on Aug. 2, 2001), 2 pages.

Feynman, R.P. et al. (1964). "Chapter 32: Refractive Index of Dense Materials" The Feyman Lectures on Physics: Mainly Electromagnetism and Matter. Addison-Wesley: Publishing Company, Inc., Reading, Massachusetts: pp. 31-1-32-13.

Finlay, W. H. (2001). "The Mechanics of Inhaled Pharmaceutical Aerosols", Academic Press: San Diego Formula 2.39. pp. 3-14 (Table of Contents), pp. v-viii.

Gonda, I. (1991). "Particle Deposition in the Human Respiratory Tract,"Chapter 176, The Lung: Scientific Foundations. Crystal R.G. and West, J.B. (eds), Raven Publishers, New York. pp. 2289-2294.

Graves, D. A. et al. (1983). "Patient-Controlled Analgesia," Annals of Internal Medicine. 99:360-366.

Hatsukami D., et al. (May 1990) "A Method for Delivery of Precise Doses of Smoked Cocaine-Base to Human." Pharmacology Biochemistry & Behavior. 36(1):1-7.

Heyder, J. et al. (1986). "Deposition of Particles in the Human Respiratory Tract in the Size Range 0.005-15 μm," J. Aerosol Sci. 17(5):811-822.

Huizer, H. (1987). "Analytical Studies on Illicit Heron. V. Efficacy of Volitization During Heroin Smoking." Pharmaceutisch Weekblad Scientific Edition. 9(4):203-211.

Hurt, R. D., MD and Robertson, C. R., PhD, (Oct. 1998). "Prying Open the Door to the Tobacco Industry's Secrets About Nicotine: The Minnesota Tobacco Trial," JAMA 280(13):1173-1181.

Hwang, S. L. (Jun. 1999). "Artificial Nicotine Studied: R. J. Reynolds Seeks to Develop Drugs that Minic Tobacco's Potent Effects on Brain," Wall Street Journal, 3 pages.

James, A.C. et al., (1991). "The Repiratory Tract Deposition Model Proposed by the ICRP Task Group," Radiation Protection Dosimetry, 38(1/3):159-165.

Kim, M. H. and Patel, D.V. (1994). "'BOP' As a Reagent for Mild and Efficient Preparation of Esters," Tet. Letters 35:5603-5606.

Lichtman, A. H. et al. (1996). "Inhalation Exposure to Volatilized Opioids Produces Antinociception in Mice," Journal of Pharmacology and Experimental Therapeutics. 279(1):69-76 XP-001118649.

Lichtman, A. H. et al. (2000). "Pharmacological Evaluation of Aerosolized Cannabinoids in Mice" European Journal of Pharmacology, vol. 399, No. 2-3: 141-149.

Lopez, K. (Jul. 1999). "UK Researcher Develops Nicotinic Drugs with R. J. Reynolds," located at <http://www.eurekalert.org/pub_releases/1999-07/UoKM-Urdn-260799.php> (visited on Oct. 1, 2002), 1 page.

Martin, B. R. and Lue, L. P. (May/Jun. 1989). "Pyrolysis and Volatilization of Cocaine," Journal of Analytical Toxicology 13:158-162.

Mattox, A.J. and Carroll, M.E. (1996). "Smoked Heroin Self-Administration in Rhesus Monkeys," Psychopharmacology 125:195-201.

McCormick, A.S.M., et al., "Bronchospasm During Inhalation of Nebulized Midazolam," British Journal of Anesthesia, vol. 80 (4), Apr. 1988, pp. 564-565 XP001119488.

Meng, Y. et al. (1997). "Inhalation Studies with Drugs of Abuse", NIDA Research Monogragh 173:201-224.

Meng, Y., et al. (1999). "Pharmacological effects of methamphetamine and other stimulants via inhalation exposure," Drug and Alcohol Dependence. 53:111-120.

Pankow, J. (Mar. 2000). ACS Conference-San Francisco-Mar. 26, 2000. Chemistry of Tobacco Smoke. pp. 1-8.

Pankow, J. F. et al. (1997). "Conversion of Nicotine in Tobacco Smoke to Its Volatile and Available Free-Base Form through the Action of Gaseous Ammonia," Environ. Sci. Technol. 31:2428-2433.

Poochikian, G. and Bertha, C.M. (2000). "Inhalation Drug Product Excipient Controls: Significance and Pitfalls," Resp. Drug Deliv. VII: 109-115.

ScienceDaily Magazine, (Jul. 1999). "University of Kentucky Researcher Develops Nicotinic Drugs with R. J. Reynolds," located at <http://www.sciencedaily.com/releases/1999/07/990728073542.htm.> (visited on Sep. 23, 2002), 2 pages.

Seeman, J. et al. (1999). "The Form of Nicotine in Tobacco. Thermal Transfer of Nicotine and Nicotine Acid Salts to Nicotine in the Gas Phase," J. Agric. Food Chem. 47(12):5133-5145.

Sekine, H. and Nakahara, Y. (1987). "Abuse of Smoking Methamphetamine Mixed with Tobacco: 1. Inhalation Efficiency and Pyrolysis Products of Methamphetamine," Journal of Forensic Science 32(5):1271-1280.

Streitwieser, A. and Heathcock, C. H. eds., (1981). Introduction to Organic Chemistry. Second edition, Macmillan Publishing Co., Inc., New York, pp. ix-xvi. (Table of Contents).

Tsantilis, S. et al. (2001). "Sintering Time for Silica Particle Growth," Aerosol Science and Technology 34:237-246.

*Vapotronics, Inc.* (1998) located at http://www.vapotronics.com.au/banner.htm., 11 pages, (visited on Jun. 5, 2000).

Vaughan, N.P. (1990). "The Generation of Monodisperse Fibres of Caffeine" J. Aerosol Sci. 21(3): 453-462.

Ward, M. E. MD, et al. (Dec. 1997). "Morphine Pharmacokinetics after Pulmonary Administration from a Novel Aerosol Delivery System," Clinical Pharmocology & Therapeutics 62(6):596-609.

Williams, S. (Feb. 1999). "Rhone-Poulenc Rorer Inc. and Targacept Inc. Announce Alliance to Develop New Drugs to Treat Alzheimer's and Parkinson's Diseases" located at http://www.rpr.rpna.com/ABOUT_RPR/pressrels/1999/990209-targa.html (last visited on Jan. 28, 2000) 1 page.

Wood, R.W. et al. (1996). "Methylecgonidine Coats the Crack Particle." Pharmacology Biochemistry & Behavior. 53(1):57-66.

Wood, R.W. et al. (1996). "Generation of Stable Test Atmospheres of Cocaine Base and Its Pyrolyzate, Methylecgonidine, and Demonstration of Their Biological Activity." Pharmacology Biochemistry & Behavior. 55(2):237-248.

\* cited by examiner

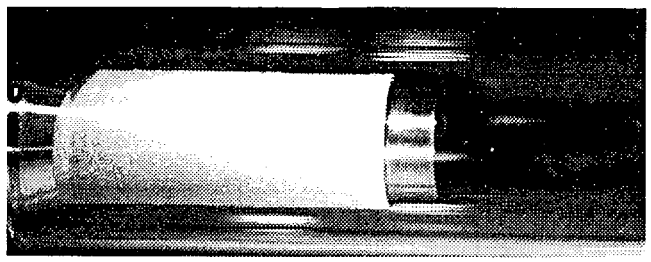
Fig. 7A    $t = 0$ ms
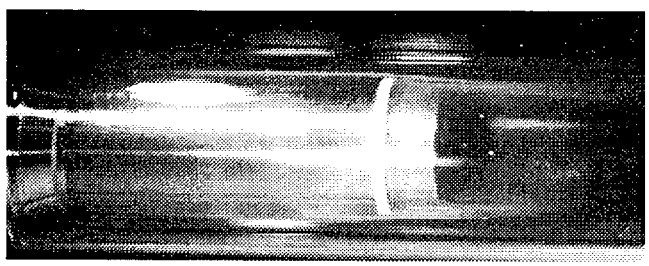
Fig. 7B    $t = 50$ ms
Fig. 7C    $t = 100$ ms
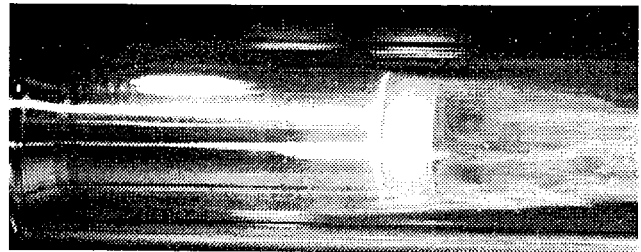
Fig. 7D    $t = 200$ ms
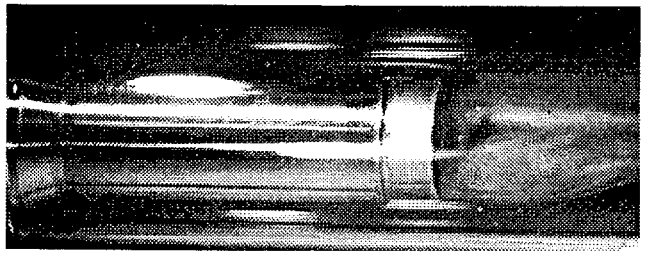
Fig. 7E    $t = 500$ ms

INHALATION DEVICE FOR PRODUCING A DRUG AEROSOL

This application claims the benefit of U.S. provisional application Ser. No. 60/429,776 filed Nov. 27, 2002, for "Method and Apparatus for Controlling Flow of Gas over a Composition," and U.S. provisional application Ser. No. 60/429,586, filed Nov. 27, 2002 for "Flow-Actuated Medical Device." Both of these applications are incorporated herein by reference in their entirety.

FIELD OF THE INVENTION

The present invention relates to an inhalation device for producing desired-size drug-aerosol particles for inhalation.

BACKGROUND OF THE INVENTION

Therapeutic compounds may be administered by a variety of routes, depending on the nature of the drug, the pharmacokinetic profile desired, patient convenience, and cost, among other factors. Among the most common routes of drug delivery are oral, intravenous (IV), intramuscular (IM) intraperitoneal (IP) subcutaneous, transdermal, transmucosal, and by inhalation to the patient's respiratory tract.

The inhalation route of drug administration offers several advantages for certain drugs, and in treating certain conditions. Since the drug administered passes quickly from the respiratory tract to the bloodstream, the drug may be active within a few minutes of delivery. This rapid drug effect is clearly advantageous for conditions like asthma, anaphylaxis, pain, and so forth where immediate relief is desired.

Further, the drug is more efficiently utilized by the patient, since the drug is taken up into the bloodstream without a first pass through the liver as is the case for oral drug delivery. Accordingly, the therapeutic dose of a drug administered by inhalation can be substantially less, e.g., one half that required for oral dosing.

Finally, since inhalation delivery is convenient, patient compliance can be expected to be high.

As is known, efficient aerosol delivery to the lungs requires that the particles have certain penetration and settling or diffusional characteristics. For larger particles, deposition in the deep lungs occurs by gravitational settling and requires particles to have an effective settling size, defined as mass median aerodynamic diameter (MMAD), of between 1-3.5 µm. For smaller particles, deposition to the deep lung occurs by a diffusional process that requires having a particle size in the 10-100 nm, typically 20-100 nm range. Particle sizes that fall in the range between 10-100 nm and 1-3.5 µm tend to have poor penetration and poor deposition. Therefore, an inhalation drug-delivery device for deep lung delivery should produce an aerosol having particles in one of these two size ranges.

Another important feature of an aerosol delivery device is control over total dose delivered, that is, the amount of aerosol generated should be predictable and repeatable from one dosing to another.

Other desirable features for an inhalation device are good product storageability, without significant loss of drug activity.

It would therefore be desirable to provide an aerosol inhalation device that provides these features in a simple, easily operated inhalation device.

SUMMARY OF THE INVENTION

The invention includes a device for delivering a drug by inhalation or by nasal administration, in an aerosol form composed of drug-particles having desired sizes, typically expressed as mass median aerodynamic diameter (MMAD) of the aerosol particles. As used herein, an aerosol is a collection of tiny solid or liquid particles that are finely dispersed in a gas. The device includes a body defining an interior flow-through chamber having upstream and downstream chamber openings. A drug supply unit contained within the chamber is designed for producing, upon actuation, a heated drug vapor in a condensation region of the chamber adjacent the substrate and between the upstream and downstream chamber openings, such that gas drawn through the chamber region at a selected gas-flow rate is effective to condense drug vapor to form drug condensation particles having a selected MMAD particle size, for example, when used for deep-lung delivery, between 10-100 nm or between 1-3.5 µm. To this end, the device includes a gas-flow control valve disposed upstream of the drug-supply unit for limiting gas-flow rate through the condensation region to the selected gas-flow rate, for example, for limiting air flow through the chamber as air is drawn by the user's mouth into and through the chamber. Also included is an actuation switch for actuating the drug-supply unit, such that the unit can be controlled to produce vapor when the gas-flow rate through the chamber is at the selected flow rate or within a selected flow-rate range.

The actuation switch may activate the drug-supply unit such that the unit is producing vapor when the selected air-flow rate is achieved; alternatively, the actuation switch may activate the drug-supply unit after the selected air-flow rate within the chamber is reached.

In one general embodiment, the gas-flow valve is designed to limit the rate of air flow through the chamber, as the user draws air through the chamber by mouth. In a specific embodiment, the gas-flow valve includes an inlet port communicating with the chamber, and a deformable flap adapted to divert or restrict air flow away from the port increasingly, with increasing pressure drop across the valve. In another embodiment, the gas-flow valve includes the actuation switch, with valve movement in response to an air pressure differential across the valve acting to close the switch. In still another embodiment, the gas-flow valve includes an orifice designed to limit airflow rate into the chamber.

The device may also include a bypass valve communicating with the chamber downstream of the unit for offsetting the decrease in airflow produced by the gas-flow control valve, as the user draws air into the chamber.

The actuation switch may include a thermistor that is responsive to heat-dissipative effects of gas flow through the chamber. The device may further include a user-activated switch whose actuation is effective to heat the thermistor, prior to triggering of the drug-supply unit by the thermistor to initiate heating of the drug-supply unit.

The drug-supply unit may include a heat-conductive substrate having an outer surface, a film of drug formed on the substrate surface, and a heat source for heating the substrate to a temperature effective to vaporize said drug. The heat source, may be, for example, an electrical source for producing resistive heating of the substrate, or a chemical heat source for producing substrate heating by initiation of an exothermic reaction. Preferably, the drug delivery unit is effective to vaporize the film of drug, following actuation, within a period of less than 1 second, more preferably, within 0.5 seconds. As used herein, vaporize and vaporization refer to the transformation of solids or liquids into gases.

For producing condensation particles in the size range 1-3.5 µm MMAD, the chamber may have substantially smooth-surfaced walls, and the selected gas-flow rate may be in the range of 4-50 L/minute.

For producing condensation particles in the size range 20-100 nm MMAD, the chamber may provide gas-flow barriers for creating air turbulence within the condensation chamber. These barriers are typically placed within a few thousands of an inch from the substrate surface.

These and other objects and features of the invention will become more fully apparent when the following detailed description of the invention is read in conjunction with the accompanying drawings.

BRIEF DESCRIPTION OF THE DRAWINGS

FIGS. 7A-7E are photographic reproductions showing the development of aerosol particles in the device over a period of about 500 msec.

DETAILED DESCRIPTION OF THE INVENTION

Figure 1:
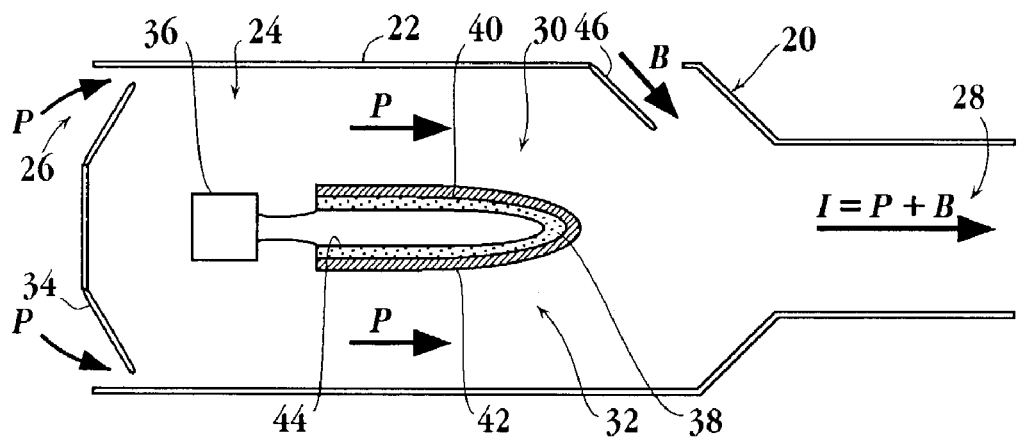
FIG. 1 is a simplified sectional view of an inhalation device constructed according to one embodiment of the invention.

FIG. 1 is a simplified cross-sectional view of an inhalation device 20 for delivering a drug by inhalation. The device includes a body 22 defining an interior flow-through chamber 24 having upstream and downstream chamber openings 26, 28, respectively. A drug-supply unit 30 contained within the chamber is operable, upon actuation, to produce a heated drug vapor in a condensation region 32 of the chamber adjacent the substrate and between the upstream and downstream chamber openings. As will be detailed below, when gas is flowed across the surface of the drug-supply unit, with either laminar flow or with turbulence, at a selected velocity, the drug vapor condenses to form drug condensation particles having a selected MMAD particle size. As one of skill in the art would appreciate, the gas velocity through the chamber may be controlled by changing the volumetric gas-flow rate, cross-sectional area within the chamber, and/or the presence or absence of structures that produce turbulence within the chamber. For inhalation, two exemplary size ranges are between about 1 and 3.5 μm, and within 0.02 and 0.1 μm.

The device includes a gas-flow control valve 34 disposed in or adjacent the upstream opening of the chamber for limiting gas-flow rate through the chamber's condensation region to a selected gas-flow rate. Typically, the gas flowed through the chamber is air drawn through the chamber by the user's mouth, that is, by the user drawing air through the upstream end of the device chamber. Various types of gas-flow valves suitable for use in the invention are described below with respect to FIGS. 5A-5F.

Also included in the device is an actuation switch, indicated generally at 36, for actuating the drug-supply unit. The switch allows the drug-supply unit to be controlled to produce vapor when the air-flow rate through the chamber's condensation region is at the selected flow rate. As will be seen, the switch is typically actuated by air flow through the chamber, such that as the user draws air through the chamber, vapor production is initiated when air flow through the condensation region reaches the selected air flow rate for producing desired-size condensation particles. Various types of activation switches suitable for use in the invention are described below with respect to FIGS. 6A-6C.

In one general embodiment, the switch is constructed to activate the drug-supply unit prior to the gas-flow rate in the chamber reaching the selected rate. In this embodiment, the timing of actuation is such that the drug-supply unit begins its production of drug vapor at about the time or after the gas-flow through the chamber reaches its selected gas-flow flow rate. In another embodiment, the drug-supply unit is actuated when the gas-flow rate through the chamber reaches the selected flow rate. In yet another embodiment, the drug-supply unit is actuated at some selected time after the selected flow rate has been reached.

The condensation region in the device, where heated drug vapor is condensed to form desired-size aerosol particles, includes that portion of the chamber between the drug-supply unit and the interior wall of the chamber, and may include a portion of the chamber between the downstream end of the drug-supply unit and the downstream opening of the chamber. It is in this region where gas flow is controlled to a desired rate and thus velocity during aerosol formation.

As shown schematically in FIG. 1, drug-supply unit 30 in the device generally includes a heat-conductive substrate 38 having an outer surface 40, a film 42 of the drug to be administered formed on the substrate's outer surface, and a heat source 44 for heating the substrate to a temperature effective to vaporize the drug. In the embodiment illustrated, the substrate is a tapered cylindrical canister closed at its upstream end. A preferred material for the substrate is stainless steel, which has been shown to be acceptable for drug stability.

The drug film includes the drug to be administered either in pure form, or mixed with suitable excipients. Exemplary drugs suitable for use include any drugs that can be vaporized at a temperature typically between 250-560° C. The drug is preferably one that can be vaporized with little or no drug-degradation products. As has been reported in several co-owned applications, many classes of drugs can be successfully vaporized with little or no degradation, particularly where the drug coating has a selected film thickness between about 0.01 and 10 μm. The amount of drug present is preferably sufficient to provide a therapeutic dose, although the device may also be used to titrate a therapeutic dose by multiple dosing. The total area of the substrate on which the film is applied may be adjusted accordingly, so that the total amount of drug available for aerosol formation constitutes a therapeutic dose. Vaporization in typically less than 0.5 seconds is enabled by the thinness of the drug coating. Essentially, the thin nature of the drug coating exposes a large fraction of the heated compound to flowing air, resulting in almost the entire compound vaporizing and cooling in the air prior to thermal degradation. At film thicknesses used in the device, aerosol particles having less than 5% degradation products are produced over a broad range of substrate peak temperatures.

The heat source for vaporizing the drug may be a resistive heating element, for example, the substrate itself, or resistive wires placed against the interior surface of the substrate.

Alternatively, and as shown in FIG. 1, heat source 44 is a chemically reactive material which undergoes an exothermic reaction upon actuation, e.g., by a spark or heat element. In the particular embodiment shown, actuation is produced by a spark supplied to the upstream end of the chemical material, igniting an exothermic reaction that spreads in a downstream to upstream direction within the drug-supply unit, that is, in the direction opposite the flow of gas within the chamber during aerosol formation. An exemplary chemical material includes a mixture of Zr and $MoO_3$, at a weight ratio of about 75%:25%. The mixture may contain binders, such as polyvinyl alcohol or nitrocellulose, and an initiator comprising additives such as boron and $KClO_3$, to control the reaction. In any case, and as mentioned above, the material should be formulated to produce complete heating over the substrate surface in a period of 2 sec or less, preferably in the range 10-500 msec.

An exemplary peak temperature of the surface of the drug-supply unit is 375° C. The temperature can be modified by changes in the fuel formulation. Because high drug purities are obtained at temperatures higher than those needed for complete vaporization, there may be a large window within which emitted dose and aerosol purity are both high and consistent.

As noted above, actuation switch 36 in the device is designed for actuating the drug-supply unit in relation to airflow through the device chamber, such that the drug-supply unit produces drug vapor when the air flow rate through the chamber is sufficient for producing desired-size aerosol particles. In one general embodiment, described below with respect to FIGS. 6A-6C, the switch is controlled by airflow through the chamber, such that the drug-supply unit is activated when (or just prior to, or after) the rate of airflow in the device reaches its desired rate. Alternatively, the switch may be user activated, allowing the user to initiate drug vapor formation as air is being drawn into the device. In the latter embodiment, the device may provide a signal, such as an audible tone, to the user, when the desired rate of airflow through the device is reached.

In the following discussion of gas-flow control through the device, it will be assumed that the gas being drawn through the device is air drawn in by the user's breath intake. However, it will be appreciated that the gas, or a portion therefore, might be supplied by a separate gas cartridge or source, such as a $CO_2$ or nitrogen gas source. An inert or non-oxidizing gas may be desirable, for example, in the vaporization of a drug that is labile to oxidative breakdown at elevated temperature, that is, during vaporization. In this case, the "gas" breathed in by the user may be a combination of a pure gas supplied through the condensation region, and air drawn in by the user downstream of the condensation region, or may be just pure gas.

In the embodiment shown in FIG. 1, airflow between the upstream and downstream ends of the device is controlled by both gas-flow valve 34, which controls the flow of air into the upstream opening of the device, and hence through the condensation region of the chamber, and a bypass valve 46 located adjacent the downstream end of the device. The bypass valve cooperates with the gas-control valve to control the flow through the condensation region of the chamber as well as the total amount of air being drawn through the device.

Figure 2A:
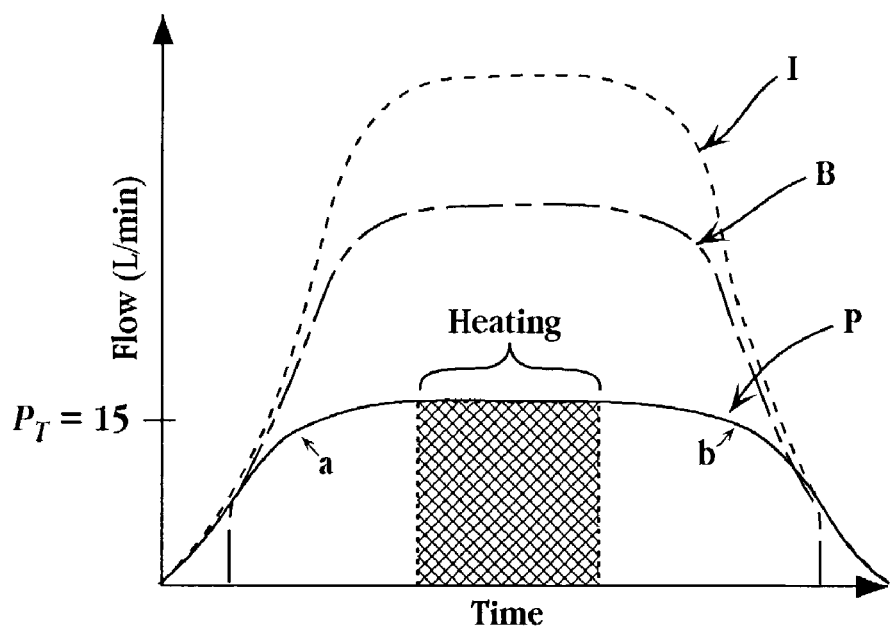
FIGS. 2A and 2B are plots of airflow rates through the device of the invention, showing airflow through primary and secondary flow regions, and the desired timing relationship between airflow level and vaporization of drug.

In particular, and as seen in the air-flow plot in FIG. 2A, the total volumetric airflow through the device, indicated at I, is the sum of the volumetric airflow rate P through valve 34, and the volumetric airflow rate B through the bypass valve. Valve 34 acts to limit air drawn into the device to a preselected level P, e.g., 15 L/minute, corresponding to the selected air-flow rate for producing aerosol particles of a selected size. Once this selected airflow level is reached, additional air drawn into the device creates a pressure drop across valve 46 which then accommodates airflow through the valve into the downstream end of the device adjacent the user's mouth. Thus, the user senses a full breath being drawn in, with the two valves distributing the total airflow between desired airflow rate P and bypass airflow rate B.

FIG. 2A also indicates the timing of the heating for the drug-supply unit, wherein the time of heating is defined as the time during which sufficient heat is applies to the drug substance so as to cause rapid vaporization of the drug. As seen here, heating time, indicated by the hatched rectangle, is intended to occur within the period that the airflow P is at the desired airflow rate, for example, within the time period indicated at points a and b in the figure. It can be appreciated that if a user draws in more or less breath, the difference in airflow rate is accommodated by changes in B, with P remaining constant as long as I is greater than P.

Figure 2B:
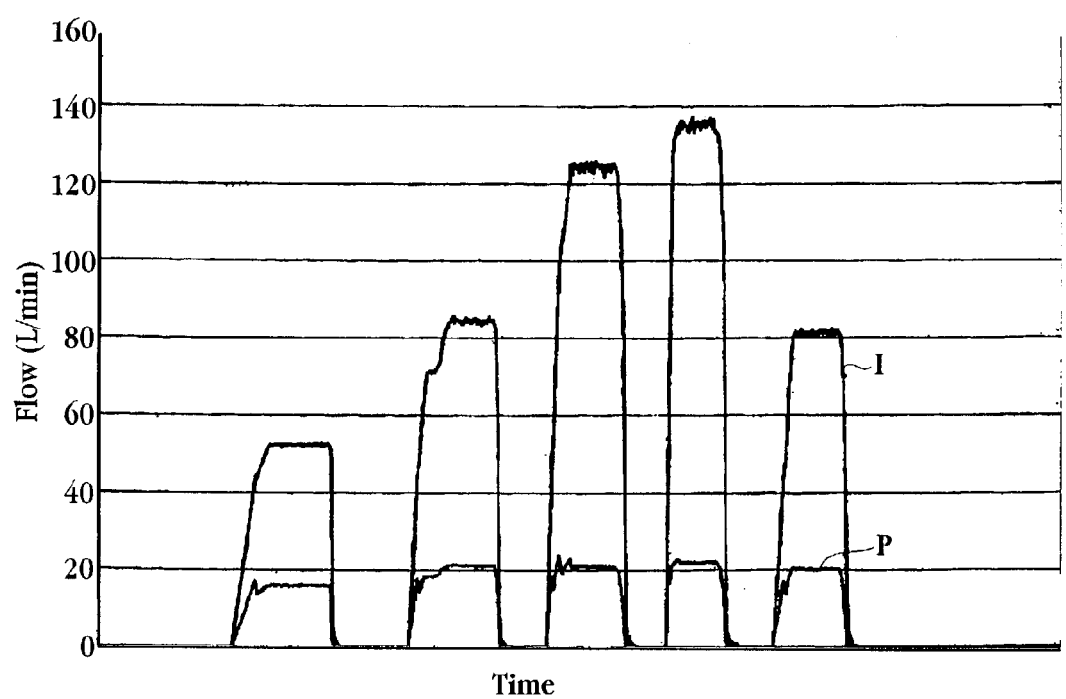

FIG. 2B shows the same gas-distribution effect, but plotted as a series of flow profiles over five different time periods during operation of the device. As seen here, the gas-flow rate through the condensation region in the device, indicated at P in the figure, remains relatively constant, while total gas-flow rate, indicated at I increases over the first four time intervals, then decreases.

Figure 4A:
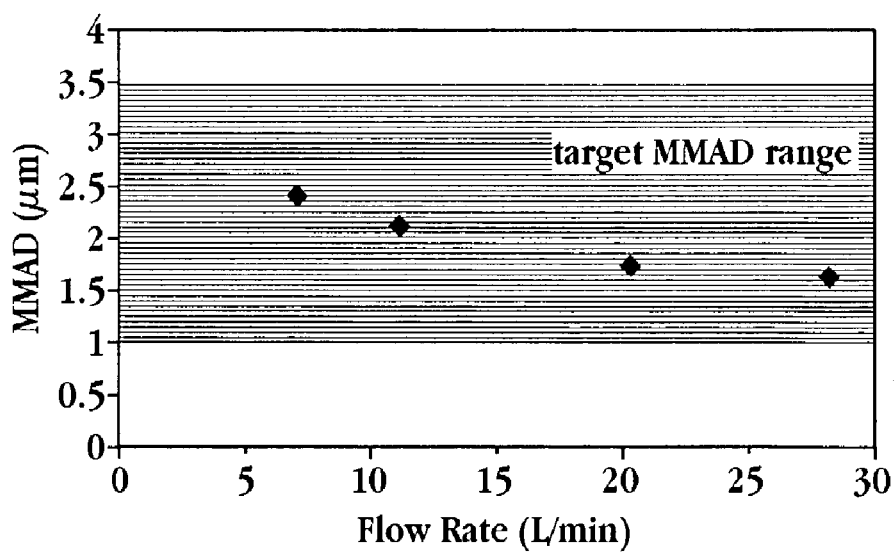
FIG. 4A is a plot of aerosol condensation particle size (MMAD) as a function of airflow rate in the absence of internal turbulence for an airflow chamber having a cross-section area of 1 cm$^2$, and at airflow rates between 5 and 30 liters/minute.

The linear velocity of airflow over the vaporizing drug affects the particle size of the aerosol particles produced by vapor condensation, with more rapid airflow diluting the vapor such that it condenses into smaller particles. In other words the particle size distribution of the aerosol is determined by the concentration of the compound vapor during condensation. This vapor concentration is, in turn, determined by the extent to which airflow over the surface of the heating substrate dilutes the evolved vapor. As shown in FIG. 4A below, the particle size (MMAD) remains well within an acceptable range (1-3.5 microns) at airflow rates from 7 L/min to 28 L/min through the drug product. To achieve smaller or larger particles, the gas velocity through the condensation region of the chamber may be altered by (i) modifying the gas-flow control valve to increase or decrease P, and/or (ii) modifying the cross-section of the chamber condensation region to increase or decrease linear gas velocity for a given volumetric flow rate.

Figure 4B:
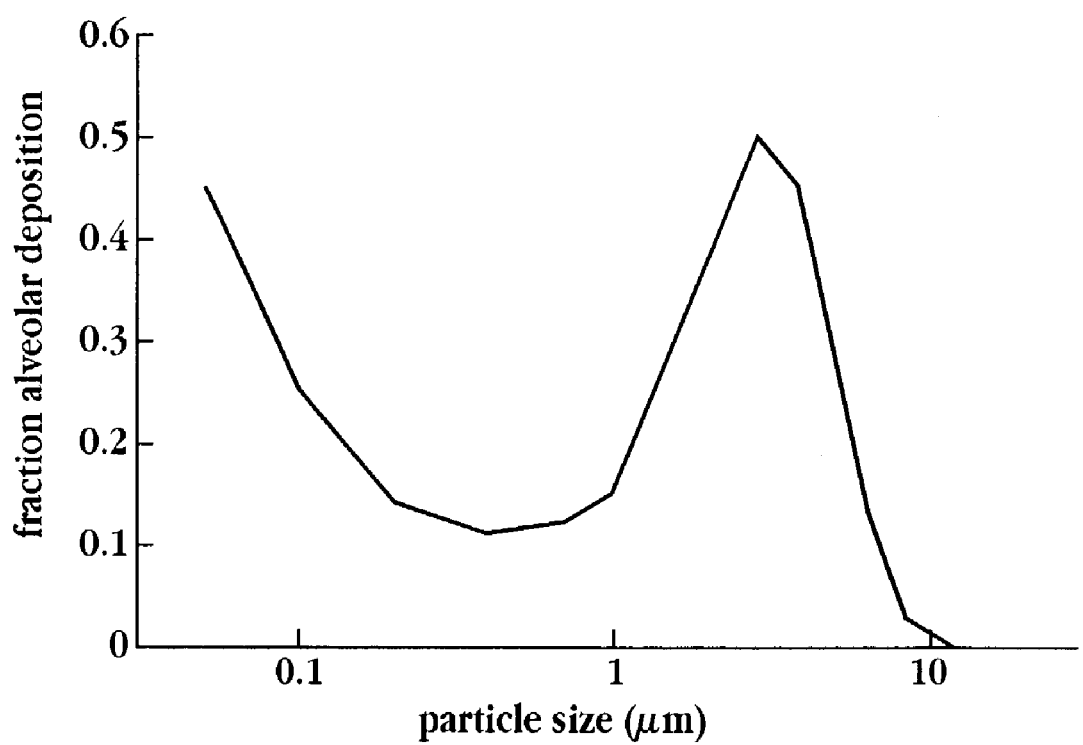
FIG. 4B shows the fraction of alveolar deposition of aerosol particles as a function of particle size.

FIG. 4B shows the fraction of alveolar deposition of aerosol particles as a function of particle size. As seen, maximum deposition into the lungs occurs in either of two size ranges: 1-3.5 µm or 20-100 nm. Therefore, where the device is employed for drug delivery by inhalation, the selected gas-flow rate in the device of a given geometry is such as to achieve aerosol particles sizes in one of these two size ranges. One skilled in the art will appreciate how changes in gas-flow velocity, to effect desired particle sizes, can be achieved by manipulating volumetric gas-flow rate, valve design and characteristics, cross-sectional area of the condensation region of the device, and, particularly where small particles are desired, placement of barriers within the chamber capable of producing turbulence that increases the dilution effect of gas flowing through the heated drug vapor.

Figure 3:
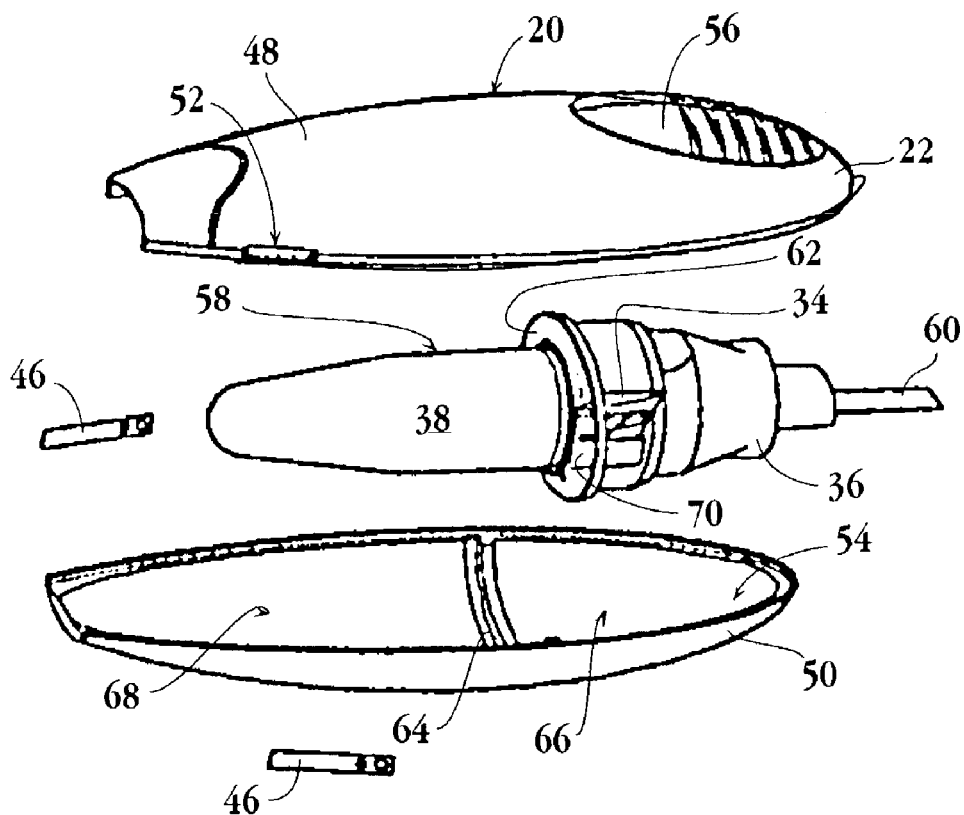
FIG. 3 is a perspective, partially exploded view of the device shown in FIG. 1.

FIG. 3 is an exploded view of device 20 illustrated in FIG. 1. Here the body of the device, indicated at 22, is formed of two molded plastic members 48, 50 which are sealed together conventionally. Bypass valves 46 are designed to be placed on either side of a downstream end region 52 of the device, when the two body members are sealed together. Member 48 includes an air inlet 56 through which air is drawn into the device chamber adjacent the upstream end of the device 54.

The drug-supply unit, air-intake valve, and actuation switch in the device are all incorporated into a single assembly 58. The parts of the assembly that are visible are the coated substrate 38, gas control valve 34, battery housing 36 and a pull tab (user-activated switch) 60 which extends through an opening at the upstream end of the device body in the assembled device. An outer flange 62 in the assembly is designed to fit in a groove 64 formed on the inner wall of each member, partitioning the chamber into upstream and downstream chamber sections 66, 68, respectively. The flange has openings, such as opening 70, formed on its opposite sides as shown, with each opening being gated by a gas-flow valve, such as valve 34, for regulating the rate of airflow across the valves. Thus, when air is drawn into the device by the user, with the user's mouth on the upstream device end, air is drawn into the device through intake 56 and into section 66. Valve 34 then regulates airflow between the two chamber sections, as will be described below with reference to FIGS. 5A-5F, to limit airflow across the drug-supply device to the desired airflow rate P.

Figure 5A:
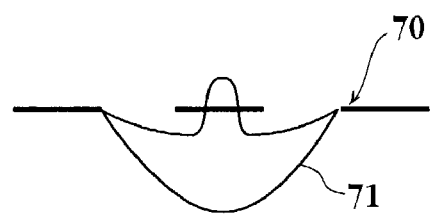
FIGS. 5A-5F illustrate different types of gas-flow valves suitable for use in the device of the invention.

Turning to various gas-flow valve embodiments suitable for the invention, FIG. 5A shows an umbrella valve 70. This valve is a low-durometer rubber member 71 that flexes out of the way to allow air to enter when the difference in pressure inside and outside of the airway (between the upstream and downstream chamber sections). This valve thus functions to "open" in response to an air pressure differential across the valve, and is constructed so that the valve limits airflow to the desired airflow rate in the device.

Figure 5B:
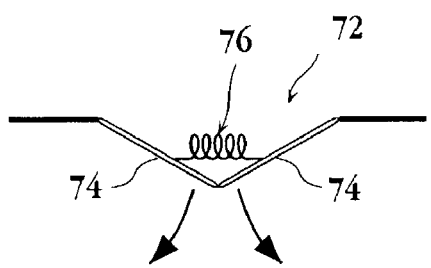

FIG. 5B illustrates a reed valve 72 that includes two low-durometer rubber pieces 74 that are held together by a biasing member 76 (such as a spring). When the air-pressure across the two chamber sections reaches a selected differential, the two rubber pieces pull apart to create an opening for air to flow into the airway. Like valve 70, this valve thus functions to "open" in response to an air pressure differential across the valve, and is constructed so that the valve limits airflow to the desired airflow rate in the device.

Figure 5C:
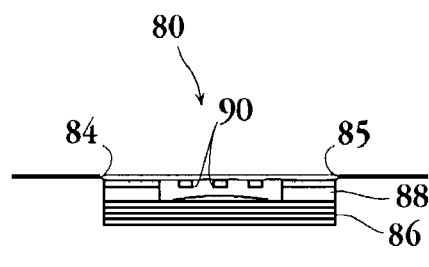
Figure 5D:
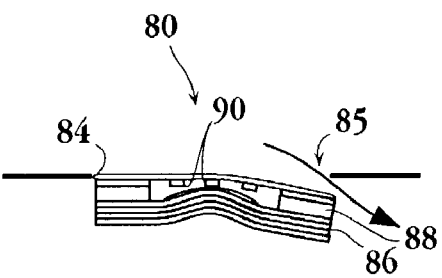

FIGS. 5C and 5D illustrate a valve 80 that bends in response to a pressure differential across the chamber sections to let air into the airway. Specifically, FIG. 5C illustrates this valve in an extended closed position that does not allow any air into the airway. One end portion of the valve is rigidly attached to a side of a valve opening 84, with the opposite side of the valve terminating against the side of an air-inlet opening 85. When the difference in pressure between the inside and outside of the airway passes a threshold level, the valve 80 bends at its center, and rotates into the airway about the portion that stays rigidly attached to the airway, as shown in FIG. 5D, creating the airway to create an orifice for air to flow through the valve opening.

In construction, the lower flexing layers at 86 are formed of flexible polymer plate material, while the upper short layers at 88 are formed of an inflexible polymer material. Also as shown, the valve may include electrical contacts, such as contact 90, that are brought into a closed circuit configuration when the valve is moved to its open, deformed condition. Like the two valves above, valve 80 functions to "open" in response to an air pressure differential across the valve, and is constructed so that in the open condition, the valve limits airflow to the desired airflow rate in the device.

The electrical switch in the valve may serve as a switching member of the actuation switch, so that opening of the valve also acts to actuate the drug-supply unit. The present invention contemplates a gas-control valve that includes an electrical switch that is moved from an open to closed condition, when the valve is moved to a condition that admits airflow at the selected desired rate.

Figure 5E:
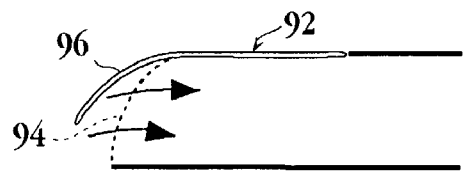
Figure 5F:
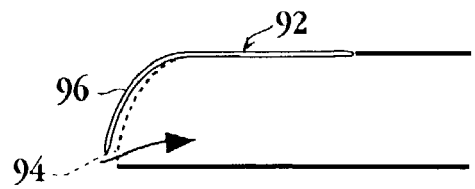

FIGS. 5E and 5F illustrate a valve 92 that moves from an open toward a partially closed condition as air is drawn into the device. The valve includes a curved screened opening 94 having a generally circular-arc cross section. A deformable valve flap 96 attached as shown at the top of the valve is designed to move toward opening 94 as the pressure differential across the valve increases, effectively closing a portion of the valve opening as the air differential increases. The deformability of the flap, in response to an air pressure differential across the valve, is such as to maintain the desired air flow rate P through the valve substantially independent of the pressure differential across the valve. The valve differs from those described above in that the valve is initially in an open condition, and moves progressively toward a closed condition as the pressure differential across the valve increases.

It will be appreciated that the bypass valve in the device may have the same general construction as one of the valves noted above, particular those valves that are designed to open when a pressure differential is applied across the valve. The gas-control and bypass valves are designed so that initial pressure differential across the valves, when the user begins drawing air into the device, is effective to first establish the desired flow rate P through the condensation region in the device. Once this flow rate is established, additional flow rate B applied by the user is effective to "open" the bypass valve to allow bypass airflow into the device. Since air is being drawn through the device along both airflow paths, the user is unaware of the bifurcation of airflow that occurs.

Figure 6A:
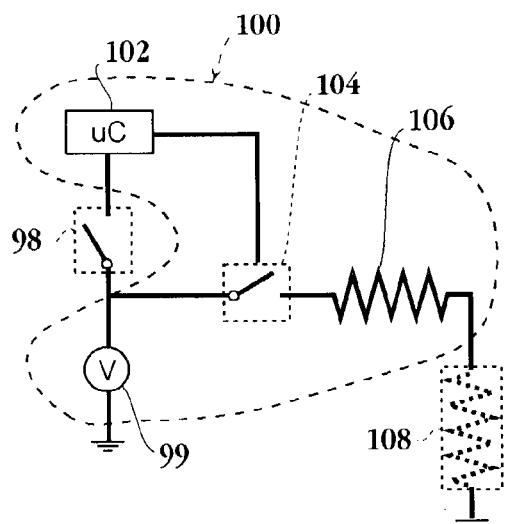
FIGS. 6A-6C illustrate different types of actuation circuitry suitable for use in the device of the invention.
Figure 6B:
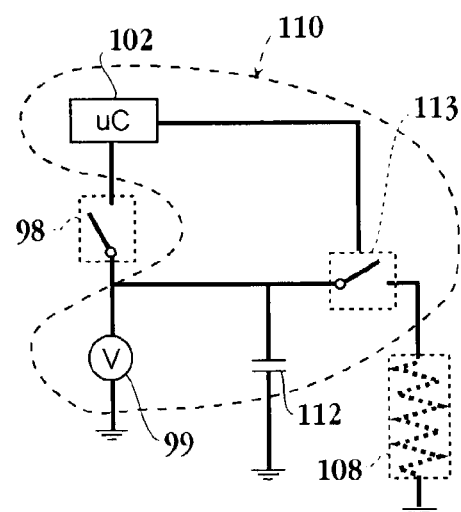
Figure 6C:
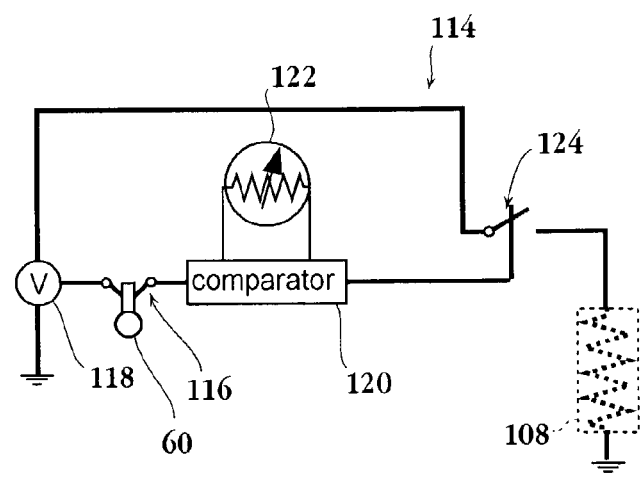

Exemplary actuation switches and associated circuitry suitable for use in the invention are illustrated in FIGS. 6A-6C. FIG. 6A illustrates a circuit 100 having a trigger switch 98 that is connected between a voltage source 99 and microcontroller 102. The trigger switch may be a valve-actuated switch, as above, or a user activated switch that is activated during air intake. When the trigger switch opens, the microcontroller no longer receives the voltage from the voltage source. Accordingly, the microcontroller senses the trigger event, and starts to measure (e.g., starts a timer) the time that the trigger event lasts. If this trigger event lasts at least the threshold time period $t_{th}$, the microcontroller closes a second switch 104 for a pulsing time interval $t_p$. This closing causes current flow from the voltage source to a resistor 106 that is effective to either heat the drug-substrate by resistive heating or to heat-initiate an exothermic reaction in the drug-supply unit, shown at 108.

FIG. 6B illustrates another circuit 110 that can be used for actuating the drug-supply unit, in accordance with the invention. This circuit is similar to circuit 100, except that it operates to pass a charge from a capacitor 112 to substrate 108. The capacitor is typically charged by voltage source 99. The microcontroller 102 closes the normally open switch 113 when it detects that switch 98 has remained open for a threshold time period. The closing of switch 113 transfers the charge from capacitor 112 to ground through the substrate. The transferred charge is used either to heat the substrate resistively, or to initiate an exothermic reaction in the drug-supply unit as above.

Another exemplary actuation switch is illustrated at 114 in FIG. 6C. This switch has a user-activated component which readies the switch for use shortly before use, e.g., an air-flow responsive component that activates the drug-supply unit when the desired air-flow rate is achieved. The user-activated component is a pull-tab switch 116 that is activated when the user pulls a tab (tab 60 in the device illustrated in FIG. 3).

When switch 116 is closed, voltage source 118 is connected to a thermistor 122 which is then heated to a temperature above ambient. The thermistor is connected to a voltage comparator 120, such as a Seiko S-8143 comparator available from Seiko. The comparator functions to measure the thermistor voltage output at a time shortly after the user switch is activated. When a user then begins to draw air across the thermistor, the airflow cause the thermistor to cool, generating a different voltage output (by the thermistor). When the difference in these voltages reaches a predetermined threshold, the comparator signals a solid-state switch 124 to close, producing current flow to drug-supply unit 108 from voltage source 118, and activation of the unit. The heating of the thermistor and comparator threshold are adjusted such that switch 124 is closed when the air flow rate through the device reaches a desired airflow rate.

The series of photographic reproductions in FIGS. 7A-7D illustrate the time sequence of production of drug condensate during operation of the device of the invention. At time 0 (FIG. 7A) when the drug-supply unit is first actuated, air flow is established across the surface of the substrate, but no vapor has yet been formed. At 50 msec (FIG. 7B), some condensate formation can be observed downstream of the substrate. The amount of condensate being formed increases up to about 200 msec, but is still being formed at 500 msec, although the majority of condensate has been formed in the first 500 msec.

Figure 8A:
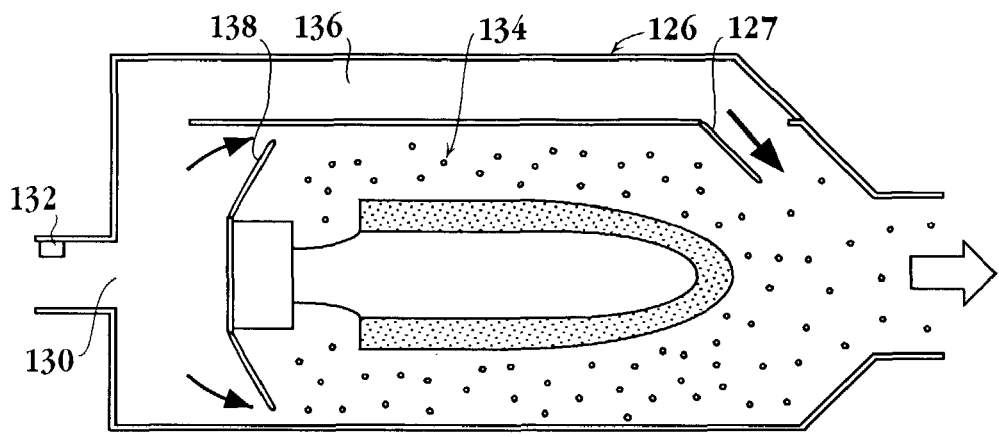
FIGS. 8A-8C show alternative airflow control configurations in the device of the invention.
Figure 8B:
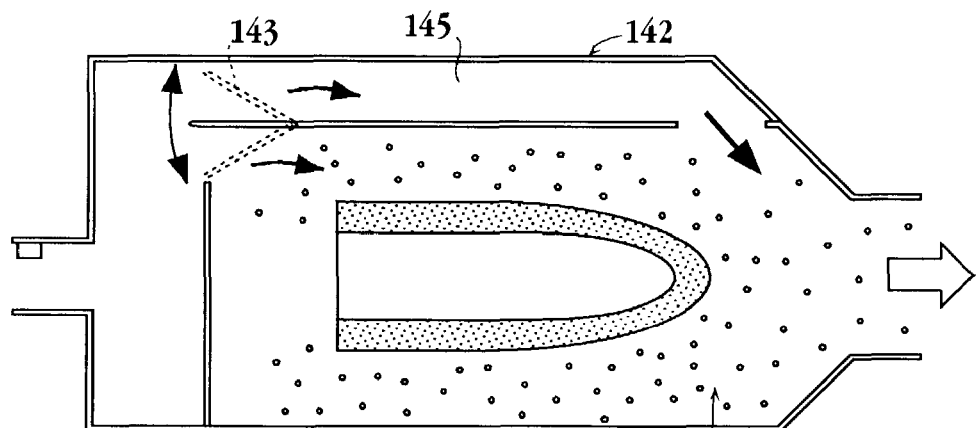
Figure 8C:
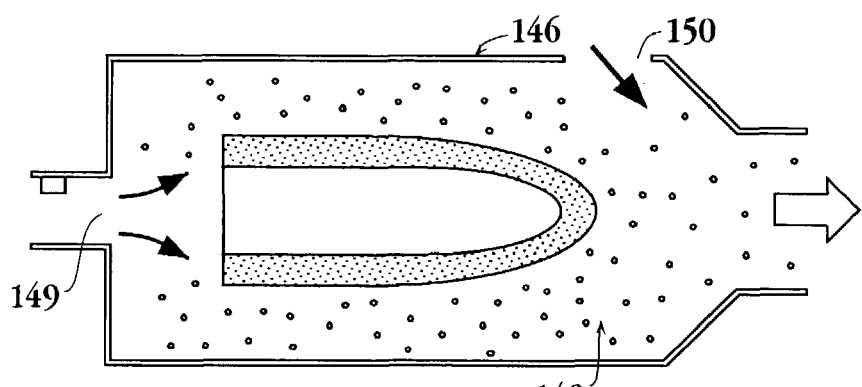

FIGS. 8A-8C illustrate alternative device embodiments for distributing airflow through the device during operation. In FIG. 8A, a device 126 includes an upstream opening 130 containing an airflow sensor 132, such as the thermistor described above, which is responsive to airflow through the opening. Air flow drawn into a central chamber 134 by the user through opening 130 is valved, to achieve a selected flow rate, by gas-flow control valve(s) 138. Excess airflow is diverted to the downstream end region of the chamber via a bypass channel 136 extending between the upstream and downstream ends of the device, and communicating with central chamber 134 through a valve 127. The orifice is so dimensioned that drawing air into the device creates an initial pressure differential across valve 138, so that airflow through the central chamber reaches the desired airflow rate, with excess air being diverted through the bypass orifice.

A device 142 shown in FIG. 8B has a similar airflow configuration, but differs from device 126 in having only a single valve 143 which functions to admit air into a central chamber 144 until a desired airflow rate is achieved, then divert excess air into a bypass channel 145 that communicates with the downstream end of the central chamber through an orifice as shown.

In the embodiment shown in FIG. 8C, and indicated at 146, air is drawn into the upstream end of the central chamber 148 through an upstream orifice 149, and is drawn into the downstream end of the chamber through a bypass orifice 150. The two orifices are dimensioned so that air drawn into the device by the user distributes at a predetermined ratio, corresponding roughly to the desired ratio of P/B (see FIG. 2A) for a normal breath intake.

It will be appreciated from the above that the gas-control valve in the device, and/or the bypass valve may include a valve that has an active gas-control element, or may be an orifice dimensioned to admit gas at a desired gas-flow rate, under conditions of selected gas pressure differential.

From the forgoing, it can be appreciated how various objects and features of the invention have been met. For use in drug inhalation, the device reproducibly produces particles having selected MMAD sizes either in the 1-3.5 μm range, or in the 10-100 nm range, achieved by controlling air flow rates through the device and the timing of airflow with respect to vapor production. Because of the rapid vapor production, and where necessary, because of the drug film thickness, the condensation particles are substantially pure, i.e., free of degradation products. The device is simple to operate, requiring little or no practice by the user to achieve desired aerosol delivery, and relatively simple in construction and operation.

Although the invention has been described with reference to particular embodiments, it will be appreciated that various changes and modifications may be made without departing from the invention.

It is claimed:

1. A device for delivering a drug by inhalation, comprising:
   a) a chamber having upstream and downstream openings;
   b) a drug supply unit that produces a drug vapor in a region of said chamber between said upstream and downstream openings;
   c) a gas-flow control valve upstream of said region that limits gas flow from a user's breath intake through said region to a selected flow rate or flow rate range, effective to condense said drug vapor to form an aerosol;
   d) a bypass orifice communicating with said chamber at a point of communication, said bypass orifice being configured to allow bypass gas to enter said chamber under conditions of inhalation actuated selected pressure differential across said bypass orifice, the point of communication preventing the bypass gas from significantly varying the selected flow rate or flow rate range through said region; and
   e) an actuation switch for causing said drug supply unit to produce said drug vapor.

2. The device of claim 1, wherein said drug supply unit is contained within said chamber.

3. The device of claim 1, wherein said drug supply unit comprises a heat source and a drug coated substrate.

4. The device of claim 1, wherein drug vapor production is initiated when said selected flow rate or flow rate range is reached.

5. The device of claim 1, wherein drug vapor production is initiated after said selected flow rate or flow rate range is reached.

6. The device of claim 1, wherein said gas-flow control valve comprises an active gas-control element.

7. The device of claim 1, wherein said gas-flow control valve is an orifice.

8. The device of claim 1, wherein said actuation switch comprises a thermistor that is responsive to heat-dissipative effects of gas flow through said chamber.

9. The device of claim 1, wherein said point of communication is downstream of said region.

10. The device of claim 1, further comprising a bypass channel in fluid communication with said bypass orifice.

11. The device of claim 1, further comprising a gas flow sensor.

12. The device of claim 1, further comprising an active gas-control element operatively associated with the bypass orifice.

13. The device of claim 1, further comprising a valve operatively associated with the bypass orifice.

14. The device of claim 1, wherein said device comprises a plurality of bypass orifices.

15. The device of claim 1, further comprising the downstream opening being configured for a user to draw air through the chamber by mouth, the bypass orifice being configured to offset a decrease in airflow produced by the gas control valve as a user draws air into the chamber.

16. The device of claim 1 wherein said device is configured to be handheld.

17. A device for delivering a drug by inhalation, comprising:
   a) a chamber having upstream and downstream ends;
   b) a drug supply unit that produces drug vapor in a region of said chamber between said upstream and downstream ends;
   c) an upstream orifice communicating with said chamber upstream of said region that limits gas flow from a user's breath intake through said region to a selected flow rate or flow rate range, effective to condense said drug vapor to form an aerosol;
   d) a bypass orifice communicating with said chamber downstream of said region that allows gas to enter said chamber under conditions of inhalation actuated selected pressure differential across said bypass orifice; and
   e) an actuation switch for causing said drug supply unit to produce drug vapor.

18. The device of claim 17, wherein said drug supply unit is contained within said chamber.

19. The device of claim 17, wherein said drug supply unit further comprises a heat source and a drug coated substrate.

20. The device of claim 17, wherein drug vapor production is initiated when said selected flow rate or flow rate range is reached.

21. The device of claim 17, wherein drug vapor production is initiated after said selected flow rate or flow rate range is reached.

22. The device of claim 17, wherein said actuation switch comprises a thermistor that is responsive to heat-dissipative effects of gas flow through said chamber.

23. The device of claim 17, further comprising a bypass channel communicating with said bypass orifice.

24. The device of claim 17, further comprising a gas flow sensor.

25. The device of claim 17, wherein said device comprises a plurality of bypass orifices.

26. A device for delivering a drug by inhalation, comprising:
   a) a chamber having upstream and downstream openings;
   b) a drug supply unit that produces a drug vapor in communication with a condensation region of said chamber between said upstream and downstream openings;
   c) a gas-flow control valve upstream of said drug supply unit that allows gas from a user's breath intake to enter said condensation region at a selected flow rate or flow rate range to produce a condensation aerosol of a select particulate size range;
   d) a bypass orifice communicating with said chamber downstream of said gas-flow control valve at a location that allows gas to enter said chamber under conditions of inhalation actuated selected pressure differential across said bypass orifice without significantly varying the selected flow rate; and
   e) an actuation switch for causing said drug supply unit to produce said drug vapor.

27. The device of claim 26, wherein said drug supply unit is contained within said chamber.

28. The device of claim 26, wherein said drug supply unit comprises a heat source and a drug coated substrate.

29. The device of claim 26, wherein drug vapor production is initiated when gas flow through said region reaches the selected flow rate or flow rate range.

30. The device of claim 26, wherein drug vapor production is initiated after gas flow through said region reaches the selected flow rate or flow rate range.

31. The device of claim 26, wherein said gas-flow control valve comprises an active gas-control element.

32. The device of claim 26, wherein said gas-flow control valve is an orifice.

33. The device of claim 26, wherein said actuation switch comprises a thermistor that is responsive to heat-dissipative effects of gas flow through said chamber.

34. The device of claim 26, wherein said bypass orifice communicates with said chamber downstream of said condensation region.

35. The device of claim 26, further comprising a bypass channel communicating with said bypass orifice.

36. The device of claim 26, further comprising a gas flow sensor.

37. The device of claim 26, further comprising an active gas-control element operatively associated with said bypass orifice.

38. The device of claim 26, further comprising a bypass valve operatively associated with the bypass orifice.

39. The device of claim 26, wherein said device comprises a plurality of bypass orifices.

40. The device of claim 26, further comprising the downstream opening being configured for a user to draw air through the chamber by mouth, the bypass orifice being configured to offset a decrease in airflow produced by the gas control valve as a user draws air into the chamber.

41. A device for delivering a drug by inhalation, comprising:
   a) a chamber having upstream and downstream ends;
   b) a drug supply unit that produces drug vapor in communication with a condensation region of said chamber between said upstream and downstream ends;
   c) an upstream orifice communicating with said chamber upstream of said condensation region that allows gas from a user's breath intake to enter said condensation region at a selected flow rate or flow rate range to produce a condensation aerosol of a select particle size range;
   (d) a bypass orifice communicating with said chamber downstream of said upstream orifice at a location that allows gas to enter said chamber under conditions of inhalation actuated selected gas pressure differential across said bypass orifice without significantly varying the selected flow rate; and
   d) an actuation switch for causing said drug supply unit to produce drug vapor.

42. The device of claim 41, wherein said drug supply unit is contained within said chamber.

43. The device of claim 41, wherein said drug supply unit further comprises a heat source and a drug coated substrate.

44. The device of claim 41, wherein drug vapor production is initiated when gas flow through said region reaches a selected flow rate or flow rate range, effective to condense said drug vapor to form an aerosol.

45. The device of claim 41, wherein drug vapor production is initiated after gas flow through said region reaches the selected flow rate or flow rate range.

46. The device of claim 41, wherein said actuation switch comprises a thermistor that is responsive to heat-dissipative effects of gas flow through said chamber.

47. The device of claim 41, wherein said bypass orifice communicates with said chamber downstream of said condensation region.

48. The device of claim 41, further comprising a bypass channel communicating with said bypass orifice.

49. The device of claim 41, further comprising a gas flow sensor.

50. The device of claim 41, wherein said device comprises a plurality of bypass orifices.

51. The device of claim 41, further comprising a bypass valve operatively associated with the bypass orifice.

* * * * *